United States Patent [19]
Sheikh et al.

[11] Patent Number: 5,968,767
[45] Date of Patent: Oct. 19, 1999

[54] METHODS FOR IN VITRO PROTEIN SYNTHESIS

[75] Inventors: Amina Sheikh, London, United Kingdom; James R. Swartz, Menlo Park, Calif.

[73] Assignee: Genentech, Inc., South San Francisco, Calif.

[21] Appl. No.: 08/870,115

[22] Filed: Jun. 5, 1997

Related U.S. Application Data

[60] Provisional application No. 60/088,354, Jun. 7, 1996, abandoned.

[51] Int. Cl.$^6$ .............................. C12P 21/00; C12N 1/00; C07K 14/00
[52] U.S. Cl. ...................... 435/68.1; 435/317.1; 435/820
[58] Field of Search ................................ 435/68.1, 317.1, 435/820; 935/17, 76

[56] References Cited

U.S. PATENT DOCUMENTS 5,492,817  2/1996  Thompson et al. .................... 435/68.1

FOREIGN PATENT DOCUMENTS

| | | |
|---|---|---|
| 401369 | 12/1990 | European Pat. Off. |
| 593757 | 4/1994 | European Pat. Off. |
| WO 94/06928 | 3/1994 | WIPO |
| WO 94/24303 | 10/1994 | WIPO |
| WO 96/14426 | 5/1996 | WIPO |
| WO 96/14428 | 5/1996 | WIPO |

OTHER PUBLICATIONS

Kigawa, T. and Yokohama, S., "Continuous Cell–Free Protein Synthesis System for Coupled Transcription–Translation" *Journal of Biochemistry* 110:166–168 (1991).

Spirin, A.S. et al., "Continuous Cell–Free Translation System Capable of Producing Polypeptides in High Yield" *Science* 242 (4882) : 1162–1164 (Nov. 25, 1988).

Baranov et al., "Gene expression in a cell–free system on the preparative scale" *Gene* 84:463–466 (1989).

Findeis and Whitesides, "Protein synthesis in cell–free reticulocyte lysates on multi–hour incubation" *Applied Biochem. Biotechnol.* 15:169–189 (1987).

Gold & Schweiger, "Synthesis of bacteriophage–specific enzymes directed by DNA in Vitro" *Meth. Enzymol.* 20:537–542 (1971).

Kawarasaki et al., "A long–lived batch reaction system of cell–free protein synthesis" *Analytical Biochemistry* 226:320–324 (1995).

Kudlicki et al., "High efficiency cell–free synthesis of proteins: refinement of the coupled transcription/translation system" *Analytical Biochemistry* 206:389–393 (1992).

Lesley, S.A. et al., "Use of in vitro protein synthesis from polymerase chain reaction–generated templates to study interaction of *Escherichia coli* transcription factors with core RNA polymerase and for epitope mapping of monoclonal antibodies" *Journal of Biological Chemistry* 266(4):2632–2638 (1991).

Pelham & Jackson, "An Efficient mRNA–Dependent Translation System from Reticulocyte Lysates" *European Journal of Biochemistry* 67:247–256 (1976).

(List continued on next page.)

*Primary Examiner*—Robert A. Wax
*Assistant Examiner*—Gabriele E. Bugaisky
*Attorney, Agent, or Firm*—Richard B. Love

[57] ABSTRACT

A method is provided for in vitro protein synthesis in a bacterial extract wherein the reaction mixture comprises a reducing agent and dissolved oxygen ($DO_2$) wherein the $DO_2$ concentration is regulated such that complete oxidation of the reducing agent concentration does not occur for a period of at least about 30 minutes following initiation of protein synthesis in the reaction mixture. Also provided is a method for in vitro protein synthesis in bacterial extracts wherein the reaction mixture comprises an initial methionine concentration of at least about 1.0 mM, or wherein the reaction mixture comprises both labeled and unlabeled methionine, and the initial concentration of unlabeled methionine is at least about 0.1 mM.

25 Claims, 5 Drawing Sheets

OTHER PUBLICATIONS

Pratt, Julie, "Coupled transcription–translation in prokaryotic cell–free systems" *Transcription & Translation: A Practical Approach,* Hames & Higgins, IRL Press, Chapter 7, pp. 179–209 (1987).

Roberts & Paterson, "Efficient translation of tobacco mosaic virus RNA and rabbit globin 9S RNA in a cell–free system from commercial wheat germ" *Proc. Natl. Acad. Sci.* 70(8) :2330–2334 (1973).

Zubay, "In vitro synthesis of protein in microbial systems" *Ann. Rev. Genet.,* Chapter 3056, 7:267–287 (1973).

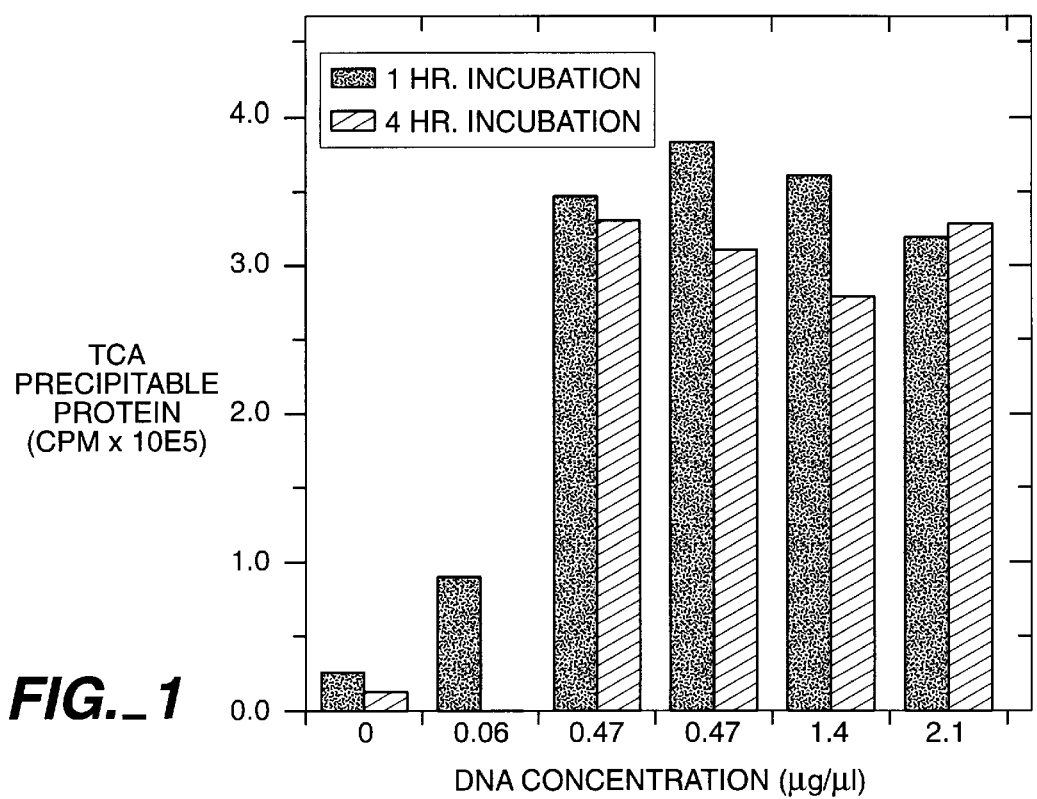
FIG._1
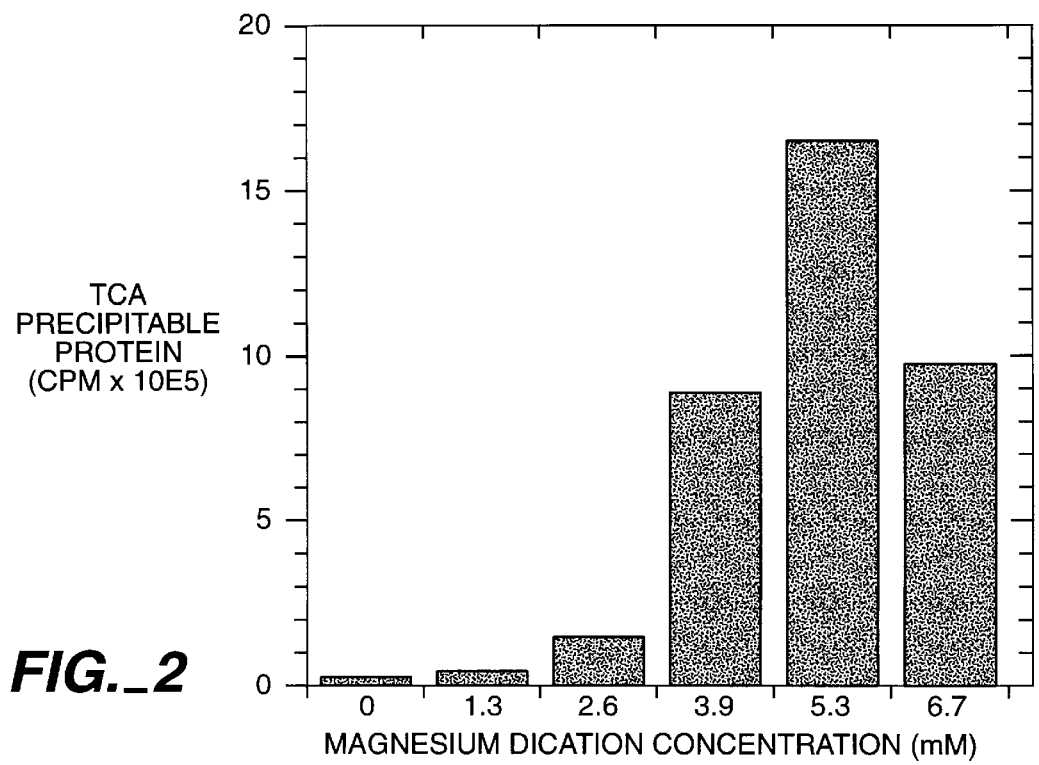
FIG._2

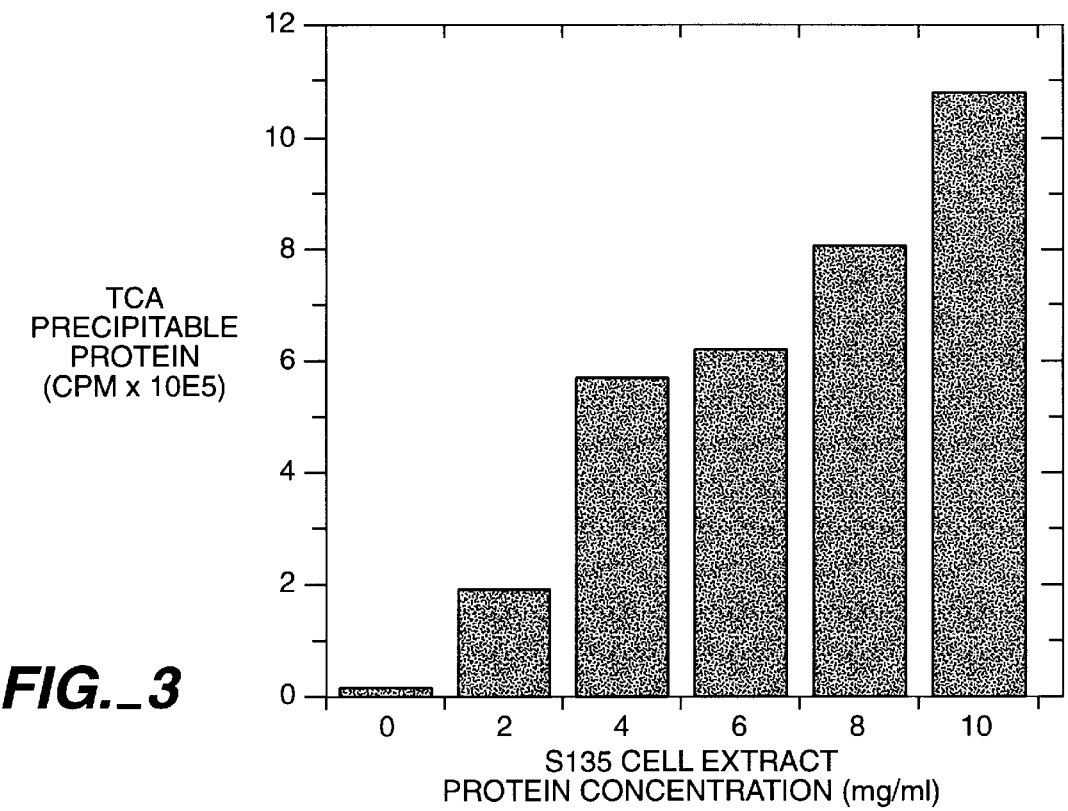
FIG._3
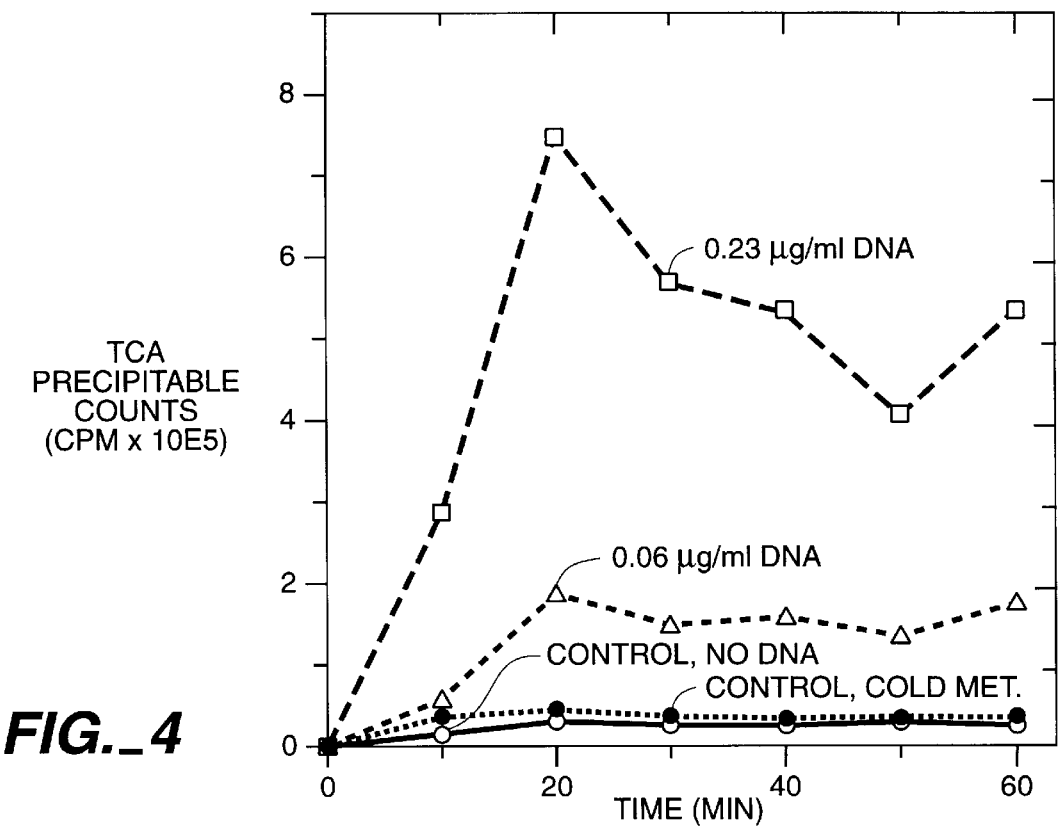
FIG._4

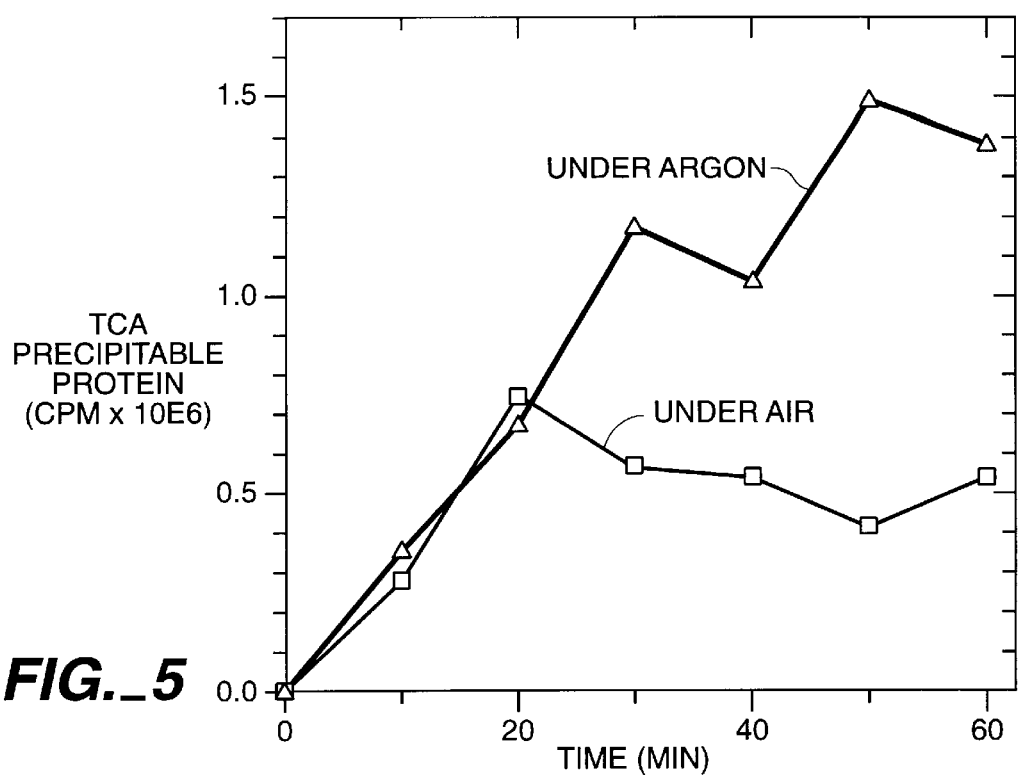
FIG._5
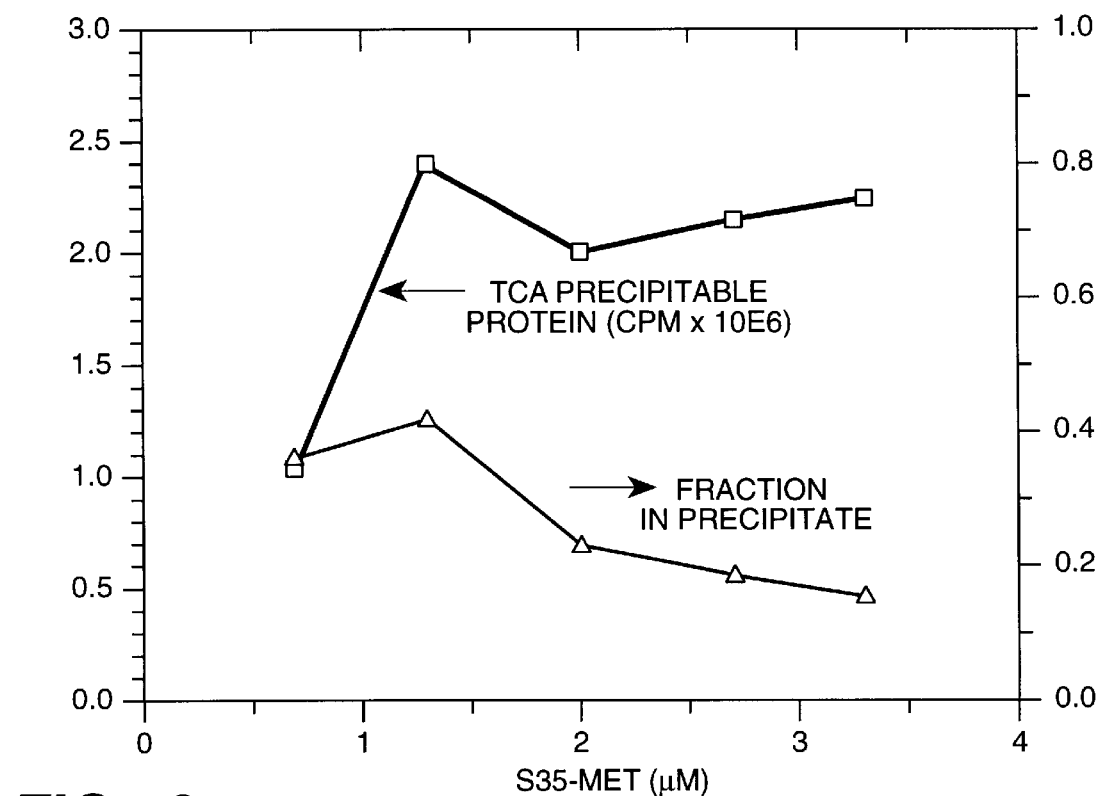
FIG._6

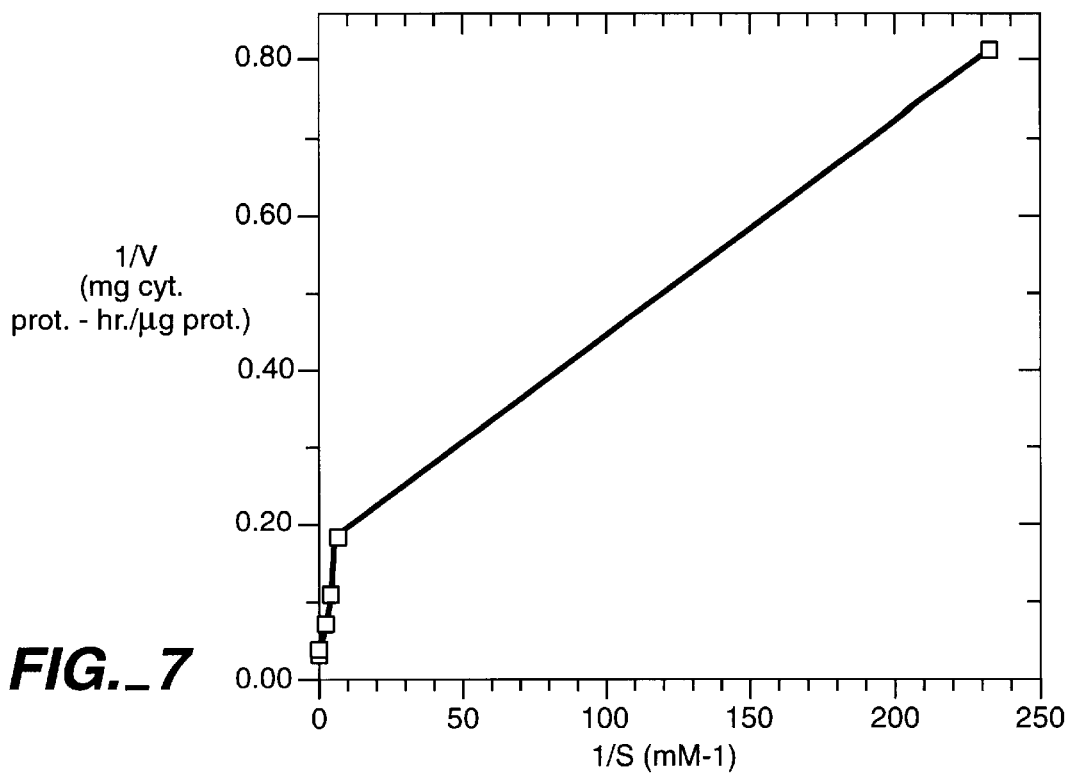
FIG._7
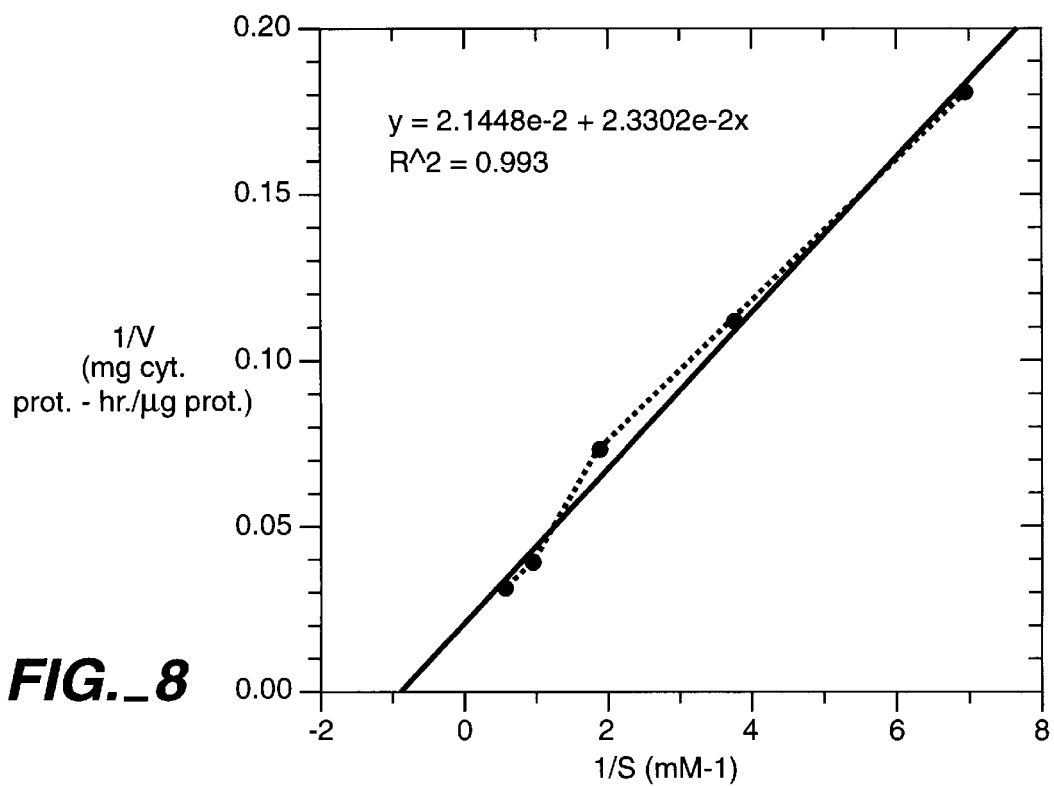
FIG._8

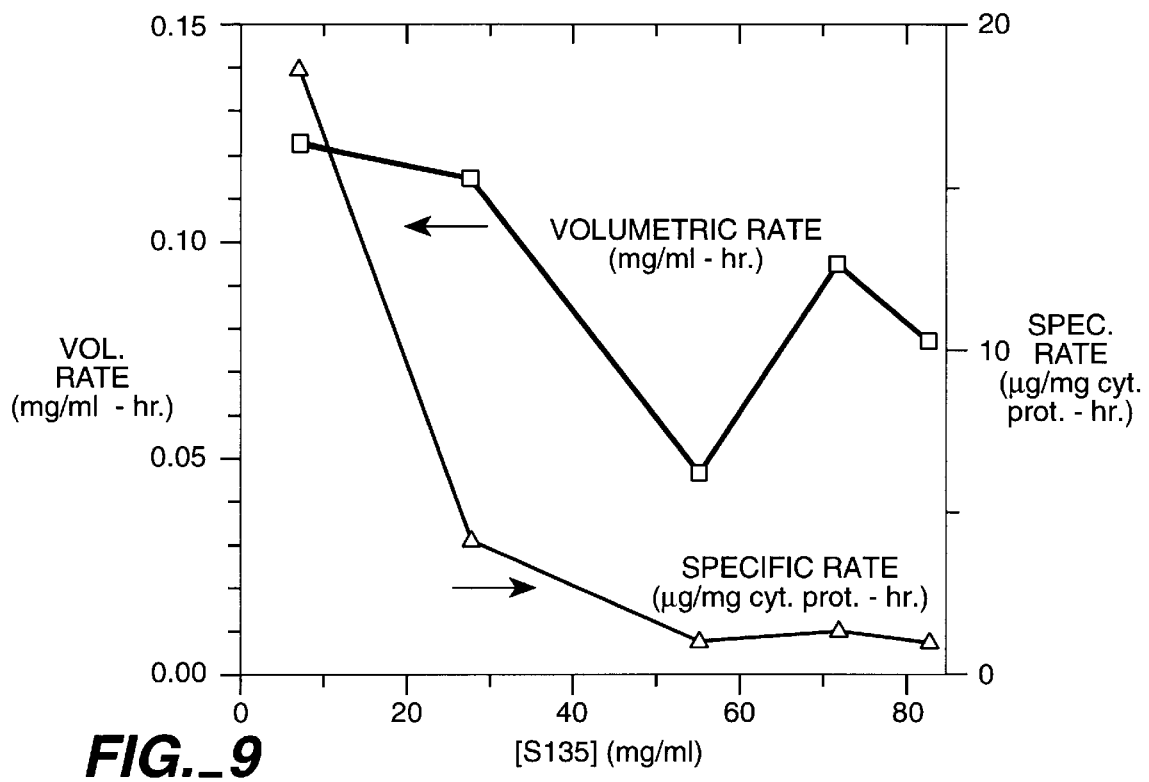
FIG._9
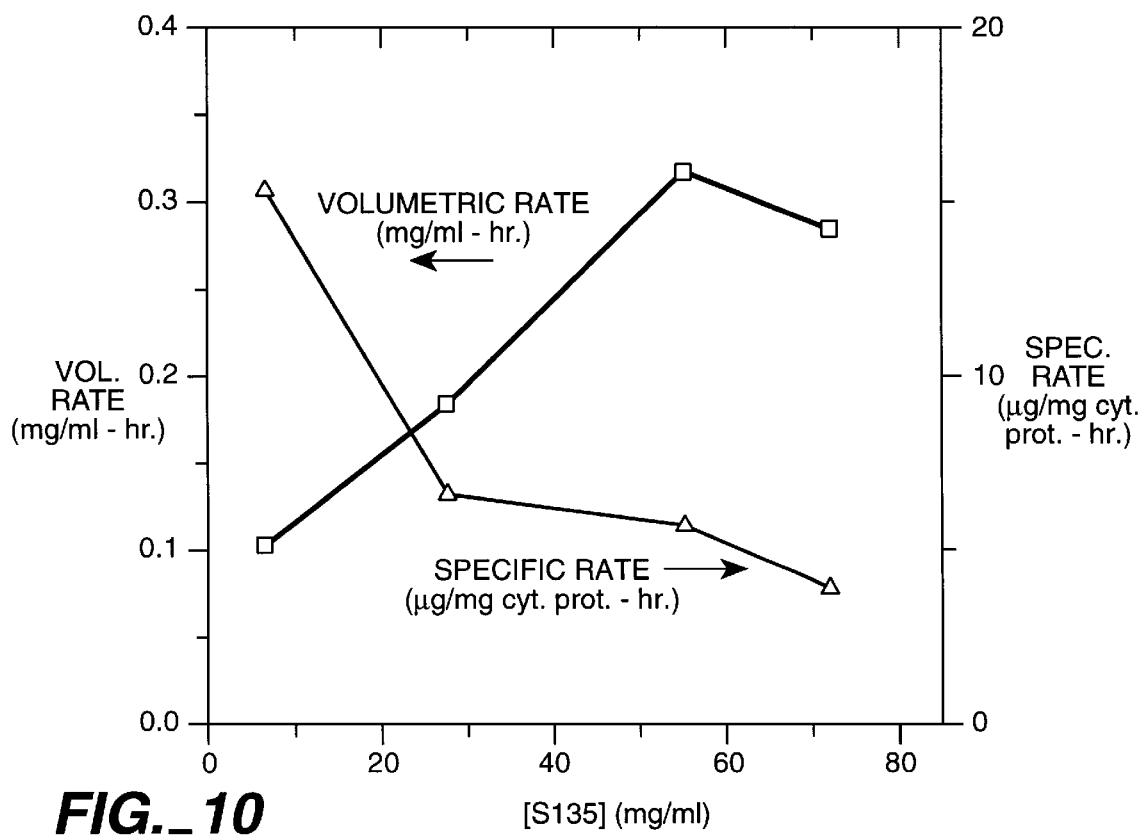
FIG._10

METHODS FOR IN VITRO PROTEIN SYNTHESIS

RELATED APPLICATIONS

This application is a non-provisional application filed under 37 CFR 1.53(b)(1), claiming priority under 35 USC 119(e) to provisional application No. 60/088,354, now abandoned, converted from non-provisional application Ser. No. 08/660,439 filed Jun. 7, 1996, the contents of which are incorporated herein by reference.

BACKGROUND OF THE INVENTION

1. Field of the Invention

This invention relates to the field of cell-free protein synthesis, and more particularly to methods and compositions for in vitro protein synthesis.

2. Description of the Background and Related Art

Cell-free translation systems have been used in the study of protein biosynthesis and have become a standard tool in molecular biology for studying messenger ribonucleic acids (RNAs) and other nucleic acids. Both eukaryotic and prokaryotic cell-free systems have been used for in vitro protein synthesis. The rabbit reticulocyte (Pelham and Jackson, *Eur. J. Biochem.*, 67: 247–256 (1976)) and wheat germ lysate (Roberts and Paterson, *Proc. Natl. Acad. Sci.*, 70: 2330–2334 (1973)) methods are commonly used eukaryotic in vitro translation systems. The *E. coli* S30 extract method devised by Zubay, *Ann. Rev. Genet.*, 7: 267 (1973) and the fractionated method of Gold and Schweiger, *Meth. Enzymol.*, 20: 537 (1971) are widely used prokaryotic in vitro translation systems.

In the case of the rabbit reticulocyte method, cell-free reticulocyte lysates continue to synthesize protein at approximately 60% of the rate of intact cells for up to one hour. Findeis and Whitesides, *Appl. Biochem. Biotechnol.*, 15: 169–189 (1987) found that the addition of extra adenosine 5'-triphosphate(ATP), guanosine 5'-triphosphate(GTP) and $Mg^{2+}$ to the lysates produced a modest gain in protein synthesis, but were unable to reduce the loss of translational activity after 2 hours and concluded that the rabbit reticulocyte method is unsuitable for preparation of gram quantities of product.

Pratt (Pratt, J. M., "Coupled Transcription-Translation in Prokaryotic Cell-Free Systems", in *Transcription and Translation: A Practical Approach*, Hames and Higgins, eds, IRL Press (1987), pp.179–209) optimized the plasmid deoxyribonucleic acid (DNA) concentration (1.6 $\mu g/\mu l$) and the $Mg^{2+}$ concentration(10–15 mM) used in the *E. coli* extract methods of Zubay (1973) and Gold and Schweiger (1971). However, the *E. coli* extract methods of Pratt (1987), Zubay (1973), and Gold and Schweiger (1971) produce a 0.3 microgram/milliliter-hour($\mu g/ml$-hr) volumetric rate of protein synthesis, approximately 5,000 fold lower than the volumetric rate achieved by in vivo synthesis of recombinant protein in *E. coli* hosts.

Lesley et al., J. Biol. Chem., 2: 2632–2638 (1991) optimized the Zubay (1973) *E. coli* extract for use with PCR fragments and other linear DNA templates by preparing the bacterial extract from a nuclease-deficient strain of *E. coli*.

Baranov et al., *Gene*, 84: 463–466 (1989) used a continuous *E. coli* extract in vitro system to obtain protein synthesis for 20 to 50 hours. In the Baranov et al. (1989) system, the reaction mixture was continuously fed with nucleotide 5'-triphosphates (NTPs), phosphoenolpyruvate (PEP) and amino acids and products were continuously removed from the reaction vessel through ultrafiltration membranes. However, the Baranov et al. system produced a volumetric rate of protein synthesis of less than 4 $\mu g/ml$-hr whereas the volumetric rate for in vivo synthesis of a recombinant protein in an *E. coli* expression host is approximately 1500 $\mu g/ml$-hr.

Kudlicki et al., Analyt. Biochem., 206: 389–393 (1992) reported a continuous flow *E. coli* extract in vitro system using a modification of the Zubay (1973) method in which circular (non-linearized) plasmid DNA is used as the template for protein synthesis and a purified ribosome fraction is used in place of bacterial extract to drive in vitro translation. In the Kudlicki et al. method, the *E. coli* (S30) extract is prepared according to Zubay (1973) and then the ribosome fraction is isolated from the S30 extract by high speed centrifugation.

SUMMARY OF THE INVENTION

The invention provides for a method for in vitro protein synthesis comprising expressing a nucleic acid encoding a desired protein in a reaction mixture comprising a bacterial cell-free extract, wherein the reaction mixture further comprises dissolved oxygen ($DO_2$) and a reducing agent wherein the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture, and recovering the desired protein from the reaction mixture.

Also provided is a composition for in vitro protein synthesis comprising a reaction mixture comprising a bacterial extract and a nucleic acid encoding a desired protein, wherein the reaction mixture further comprises dissolved oxygen ($DO_2$) and a reducing agent wherein the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture.

The invention further provides a method for in vitro protein synthesis comprising expressing a nucleic acid encoding a desired protein in a reaction mixture comprising a bacterial cell-free extract and an initial methionine (Met) concentration of at least about 1.0 millimoles/liter (mM), and recovering the desired protein from the reaction mixture. Additionally provided is a method for in vitro protein synthesis comprising expressing a nucleic acid encoding a desired protein in a reaction mixture comprising a bacterial cell-free extract, labeled methionine and unlabeled methionine, wherein the initial unlabeled methionine (Met) concentration is at least about 0.1 millimoles/liter (mM), and recovering the desired protein from the reaction mixture.

The invention also encompasses a composition for in vitro protein synthesis comprising a reaction mixture comprising a bacterial cell-free extract, a nucleic acid encoding a desired protein, and an initial methionine concentration of at least about 1.0 mM. The invention further encompasses a composition for in vitro protein synthesis comprising a reaction mixture comprising a bacterial cell-free extract, labeled methionine, unlabeled methionine, and a nucleic acid encoding a desired protein, wherein the initial unlabeled methionine concentration is at least about 0.1 mM.

BRIEF DESCRIPTION OF THE FIGURES

FIG. 1 is a graph depicting the effect of deoxyribonucleicacid (DNA) concentration on total protein synthesis as determined by the amount of trichloroacetic acid (TCA)-precipitable, radiolabeled protein recovered at various DNA concentrations. The solid bars and hatched bars represent TCA-precipitable material recovered after one hour and four hour incubations, respectively.

FIG. 2 is a graph depicting the effect of dicationic magnesium ($Mg^{2+}$) concentration on total protein synthesis as determined by the amount of TCA-precipitable, radiolabeled protein recovered at various $Mg^{2+}$ concentrations.

FIG. 3 is a graph depicting the effect of cytoplasmic protein concentration on total protein synthesis as determined by the amount of TCA-precipitable, radiolabeled protein recovered at various concentrations of S135 bacterial extract.

FIG. 4 is a graph depicting the effect of DNA concentration on the rate of protein synthesis as determined by the amount of TCA-precipitable, radiolabeled protein recovered over a time course at various DNA concentrations. Samples taken from reactions with 0.06 micrograms/milliliter ($\mu$g/ml) DNA and 0.23 $\mu$g/ml DNA are represented as open triangles and open squares, respectively. Samples taken from control reactions with no DNA and no radiolabeled methionine are represented as open circles and closed circles, respectively.

FIG. 5 is a graph depicting the effect of air removal by argon on the duration and yield of protein synthesis as determined by the amount of TCA-precipitable, radiolabeled protein recovered over a time course in reactions conducted under air or argon. Samples taken from reactions conducted under air and argon are represented as open squares and open triangles, respectively.

FIG. 6 is a graph depicting the effect of initial methionine concentration on the yield of protein synthesis as determined by the amount of TCA-precipitable, radiolabeled protein recovered after one hour of reaction with various initial methionine concentrations. TCA-precipitable, radiolabeled protein levels(shown in units of counts per minute (CPM)× $10^6$ according to the scale appearing on the left side of the graph) observed are represented as open squares.

FIG. 7 is a graph depicting the effect of initial methionine concentration on the specific rate of protein synthesis as determined by the amount of TCA-precipitable, radiolabeled and unlabeled protein recovered per milligram (mg) of S135 bacterial extract per hour ($\mu$g/mg cytopl. prot.-hr) at various initial methionine concentrations. The data were generated from samples taken after 3 minutes of reaction time.

FIG. 8 is a graph depicting the first five data points appearing in FIG. 7.

FIG. 9 is a graph depicting the effect of bacterial extract concentration on the specific and volumetric rates of protein synthesis as determined by the amount of TCA-precipitable, radiolabeled protein recovered per mg of S135 bacterial extract per hour ($\mu$g/mg cytopl. prot.-hr) and the amount of TCA-precipitable, radiolabeled protein recovered per milliliter of reaction volume per hour ($\mu$g/ml-hr), respectively, at various concentrations of S135 bacterial extract. The data were generated from samples taken after 3 minutes of reaction with 0.28 milligrams/milliliter (mg/ml) DNA.

FIG. 10 is a graph depicting the effect of bacterial extract concentration on the specific and volumetric rates of protein synthesis as determined by the amount of TCA-precipitable, radiolabeled protein recovered per mg of S135 bacterial extract per hour and the amount of TCA-precipitable, radiolabeled protein recovered per milliliter of reaction volume per hour, respectively, at various concentrations of S135 bacterial extract. The data were generated from samples taken after 3 minutes of reaction with 0.83 mg/ml DNA.

DETAILED DESCRIPTION OF THE PREFERRED EMBODIMENTS

A. Definitions

The terms "in vitro transcription-translation", "cell-free transcription-translation", "DNA template-driven in vitro protein synthesis" and "DNA template-driven cell-free protein synthesis" are used interchangeably herein and are intended to refer to any method for cell-free synthesis of a desired protein from DNA encoding the desired protein.

The terms "in vitro translation", "cell-free translation" "RNA template-driven in vitro protein synthesis" and "RNA template-driven cell-free protein synthesis" are used interchangeably herein and are intended to refer to any method for cell-free synthesis of a desired protein from ribonucleic acid (RNA) encoding the desired protein.

The terms "cell-free protein synthesis" and "in vitro protein synthesis" are used interchangeably herein and refer to both in vitro transcription-translation and in vitro translation.

The term "expressing nucleic acid encoding a desired protein" and all grammatical variants thereof refer to the synthesis of a desired or selected protein by translation of RNA encoding the protein or by coupled transcription-translation of DNA/RNA encoding the protein.

As used herein, the terms "desired protein" or "selected protein" are used interchangeably and refer generally to any peptide or protein having more than about 5 amino acids. The polypeptides may be homologous to, or preferably, may be exogenous, meaning that they are heterologous, i.e., foreign, to the bacteria from which the bacterial cell-free extract is derived, such as a human protein or a yeast protein produced in the bacterial cell-free extract. Preferably, mammalian polypeptides (polypeptides that were originally derived from a mammalian organism) are used.

Examples of mammalian polypeptides include, but are not limited to, molecules such as, e.g., renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3,-4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-1 9; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The terms "bacterial cell-free extract" and "bacterial extract" as used herein denote any preparation comprising the components of a bacterial cell's protein synthesis machinery wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), adenosine 5'-triphosphate (ATP), uridine 5'-triphosphate (UTP), cytidine 5'-triphosphate (CTP), guanosine 5'-triphosphate (GTP), $Mg^{23}$ phosphoenolpyruvate (PEP), folinic acid, nicotinamide adenine dinucleotide phosphate ($NADP^+$), flavin adenine dinucleotide (FAD), pyridoxine, 4-aminobenzoic acid (PABA), pyruvate kinase, adenosine 3',5'-cyclicmonophosphate(3',5'-cAMP), any transcription activators that are required for initiation of transcription of DNA encoding the desired protein, transfer ribonucleic acids (tRNAs), amino acids, aminoacyl-tRNA synthetases, 70S ribosomes, $N^{10}$-formyltetrahydrofolate, formylmethionine-$tRNAf^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

The term "reaction mixture" as used herein denotes a mixture comprising a bacterial extract and a nucleic acid encoding a desired protein.

The terms "product recovery" and "recovery of a desired protein" as used herein are defined as any isolation or purification of a desired protein wherein the desired protein is at least partially separated from at least one other component in the reaction mixture, for example, by organic solvent precipitation, such as methanol, ethanol or acetone precipitation, organic or inorganic salt precipitation such as trichloroacetic acid (TCA) or ammonium sulfate precipitation, nonionic polymer precipitation such as polyethylene glycol (PEG) precipitation, pH precipitation, temperature precipitation, immunoprecipitation, chromatographic separation such as adsorption, ion-exchange, affinity and gel exclusion chromatography, chromatofocusing, isoelectric focusing, high performance liquid chromatography (HPLC), gel electrophoresis, dialysis, microfiltration, and the like.

The term "polyol" as used herein denotes a hydrocarbon containing at least two hydroxyls bonded to carbon atoms. Polyols may include other functional groups. Examples of polyols useful for practicing the invention include sugar alcohols such as mannitol and trehalose, and polyethers. The term "polyether" as used herein denotes a hydrocarbon containing at least three ether bonds. Polyethers may contain other functional groups.

B. General Methods

In general, the invention provides for the maximization of three critical indicators of protein synthesis in a bacterial cell-free extract: the duration of protein synthesis in the reaction mixture, the specific rate of protein synthesis, i.e., the amount of protein synthesized with respect to the concentration of bacterial cell-free extract in the reaction mixture and the reaction time, and the volumetric rate of protein synthesis, ie., the amount of protein synthesized with respect to the reaction volume and the reaction time.

I. Methods for Optimized Cell-Free Protein Synthesis with Regulated $DO_2$

In one embodiment, the invention provides a method for extending the duration of protein synthesis in a cell-free bacterial extract by maintaining reducing conditions in the reaction mixture, wherein the reaction mixture comprises a reducing agent (or agents) and wherein the concentration of dissolved oxygen ($DO_2$) is regulated such that complete oxidation of the reducing agent concentration does not occur for a selected period of time following initiation of protein synthesis in the reaction mixture. Although the invention is not limited to a particular mechanism of action, it is believed that the regulation of dissolved oxygen levels in a bacterial extract in vitro protein synthesis reaction mixture according to the methods of the invention extends the duration of protein synthesis by approximating the reducing conditions in the bacterial cell cytoplasm and thereby preventing oxidation of essential enzyme activities. Preferably, the $DO_2$ concentration is regulated such that complete oxidation of the reducing agent concentration does not occur for a period of at least about 30 minutes, and preferably about 40 minutes, and more preferably about one hour, and still more preferably about 2 hours, following the initiation of protein synthesis in the reaction mixture.

The regulation of $DO_2$ concentration in the reaction mixture according to invention can be accomplished by any suitable technique for limiting $DO_2$ concentration in a liquid, such as removing $DO_2$ from the reaction mixture prior to or during protein synthesis, or limiting the transfer of oxygen from the atmosphere occupying the headspace of the reaction vessel to liquid phase in the reaction mixture, or any combination thereof. In one embodiment, the amount of oxygen transferred from the headspace atmosphere to liquid phase in the reaction mixture is limited by using a reduced oxygen concentration in the headspace atmosphere and/or a reduced ratio of headspace volume to reaction mixture volume in the reaction vessel (i.e. lowering the headspace volume in proportion to the reaction mixture volume present in the reaction vessel). In another embodiment, the reaction mixture is maintained under a limited oxygen atmosphere that lacks sufficient oxygen content for increasing the $DO_2$ concentration in the reaction mixture by more than about 0.75 mM upon complete transfer of the atmospheric oxygen to liquid phase in the reaction mixture.

In a further embodiment, the $DO_2$ concentration in the reaction mixture is limited by maintaining the reaction mixture under a non-oxygen atmosphere, i. e., the headspace in the reaction vessel is occupied by a non-oxygen atmosphere during the reaction. A suitable non-oxygen atmosphere for use herein is any gaseous mixture wherein: (1) the gaseous mixture consists of about zero percent oxygen $O_2$; (2) the gaseous mixture does not contain elements or molecules capable of evolving $O_2$ upon reaction with other elements or molecules present in the gaseous mixture or in the reaction mixture under the desired conditions of temperature and pressure for in vitro protein synthesis, such as about 20° C. to about 40° C. and about 0 to about 5 atmospheres (atm); and (3) the gaseous mixture does not contain transcription or translation inhibitors in quantities sufficient to inhibit transcription or translation in the reaction mixture.

Preferred non-oxygen atmospheres include gaseous mixtures comprising one or more of the following gases: $H_2$, $N_2$, $CH_4$, and inert gases such as He, Ne, Ar, Kr, Xe, and Rn, and the like. Particularly preferred are non-oxygen atmospheres composed of inert gases, such as He, Ne, Ar, Kr, Xe, and Rn, and most preferred is an argon atmosphere.

The non-oxygen atmosphere or limited-oxygen atmosphere can be sparged into the reaction vessel after the other components of the reaction mixture are in place, and the displaced air can be removed by an exhaust valve. Alternatively, the empty reaction vessel can be filled with the non-oxygen atmosphere or limited-oxygen atmosphere, followed by the addition of the reaction mixture and the removal of displaced gas. The non-oxygen atmosphere or limited-oxygen atmosphere can be maintained by substantially closing or sealing the reaction vessel for the duration of the reaction. In another embodiment, the non-oxygen atmosphere or limited-oxygen atmosphere is maintained by a continuous flow system wherein pressurized atmosphere is injected into the reaction vessel and displaced gas is released from the reaction vessel for the duration of the reaction. In order to avoid any increase in the $DO_2$ level that would be caused by gas/liquid transfer of oxygen present in a limited oxygen atmosphere, a reaction mixture maintained under a limited oxygen atmosphere is preferably subjected to no agitation or merely gentle agitation, and the limited oxygen atmosphere is not continuously sparged through the reaction mixture.

In further embodiment, the $DO_2$ level in the reaction mixture can be limited by filling the entire reaction vessel with the reaction mixture, i.e., eliminating any headspace in the vessel. In this embodiment, the reaction mixture can be agitated by any convenient means, such as a mechanically or magnetically driven stirring bar or impeller within the reaction vessel, and the like, to improve the kinetics of the transcription and/or translation reactions without increasing the $DO_2$ level in the reaction mixture. Likewise, embodiments using a non-oxygen atmosphere can benefit from the improved kinetics of an agitated reaction mixture while avoiding the damage to reaction components that agitation can cause (through excess gas/liquid interfacial area and concomitantly increased gas/liquid transfer of oxygen) in embodiments using a limited oxygen atmosphere.

In yet another embodiment, the quantity of available oxygen is substantially reduced by decreasing the pressure in the reaction vessel, e.g. by partially evacuating the reaction vessel headspace with a standard vacuum pump.

Suitable reducing agents for use herein include compounds with free sulfhydryl groups, such as dithiothreitol, dithioerythritol, β-mercaptoethanol, glutathione, thioglycolate, and cysteine. The concentration of reducing agent necessary to achieve the reducing power desired for the selected reaction time will vary according to the strength of the reducing agent, the level of $DO_2$ allowed in the reaction mixture, and the length of the reaction time. In embodiments wherein the reaction mixture is allowed an initial $DO_2$ concentration produced by ambient air saturation (approximately 0.25 mM, depending on the composition and temperature of the reaction mixture) or less and the transfer of headspace atmospheric oxygen to liquid phase in the reaction mixture is limited so that such transfer cannot result in more than about a 0.75 mM increase in $DO_2$ concentration upon complete transfer of atmospheric oxygen to liquid phase in the reaction mixture (i.e. the oxygen content in the headspace atmosphere is no greater than an amount sufficient to increase by about 0.75 mM the $DO_2$ concentration in the reaction mixture upon complete transfer of atmospheric oxygen to liquid phase), an effective reducing potential can be obtained in the reaction mixture by using dithiothreitol at an initial concentration of about 1.0 to about 2.0 mM, and preferably about 1.3 mM to about 1.8 mM, and more preferably about 1.5 mM, or dithioerythritol at an initial concentration of about 1.0 mM to about 2.0 mM, and preferably about 1.3 mM to about 1.8 mM, or β-mercaptoethanol at an initial concentration of about 1.0 mM to about 3.0 mM, and preferably about 1.3 mM to about 2.0 mM, or reduced glutathione at an initial concentration of about 1.0 mM to about 3.0 mM, and preferably about 1.3 mM to about 2.0 mM, or thioglycolate at an initial concentration of about 1.0 mM to about 3.0 mM, and preferably about 1.3 mM to about 2.0 mM, or cysteine at an initial concentration of about 1.0 mM to about 3.0 mM, and preferably about 1.3 mM to about 2.0 mM. In other embodiments, lower concentrations of a reducing agent or agents optionally can be used in conjunction with reaction mixtures containing initial $DO_2$ concentrations below the level produced by ambient air saturation and/or reaction vessel headspace atmospheres which would increase the $DO_2$ concentration in the reaction mixture by less than about 0.75 mM upon complete transfer of atmospheric oxygen to liquid phase in the reaction mixture.

Also provided for use in the methods of the invention are reaction mixtures with an initial $DO_2$ concentration produced by ambient air saturation which are maintained under a non-oxygen atmosphere or in a reaction vessel with no headspace. In such embodiments, the desired reducing potential can be obtained in the reaction mixture by using dithiothreitol at an initial concentration of about 1.0 mM to about 2.0 mM, and preferably about 1.3 mM to about 1.8 mM, and more preferably about 1.5 mM, or dithioerythritol at an initial concentration of about 1.0 mM to about 2.0 mM, and preferably about 1.3 mM to about 1.8 mM, or β-mercaptoethanol at an initial concentration of about 1.0 mM to about 3.0 mM, and preferably about 1.3 mM to about 2.0 mM, or reduced glutathione at an initial concentration of about 1.0 mM to about 3.0 mM, and preferably about 1.3 mM to about 2.0 mM, or thioglycolate at an initial concentration of about 1.0 mM to about 3.0 mM, and preferably about 1.3 mM to about 2.0 mM, or cysteine at an initial concentration of about 1.0 mM to about 3.0 mM, and preferably about 1.3 mM to about 2.0 mM. The invention further encompasses the use of lower reducing agent (or agents) concentrations in reaction mixtures which possess an initial $DO_2$ concentration below the level produced by ambient air saturation and which are maintained under a non-oxygen atmosphere or in a reaction vessel with no headspace.

1. Preparation of Bacterial Extract

A bacterial extract derived from any strain of bacteria can be used in the methods of the invention. Suitable for use herein are all eubacteria, including Gram-negative bacteria and Gram-positive bacteria. Preferred for use herein are bacteria of the Enterobacteriaceae family. The Escherichia genus of bacteria is preferred, and any species of *Escherichia coli* is particularly preferred for preparation of the cell-free bacterial extracts used in the methods of the invention.

In a preferred embodiment, the bacterial extract is derived from a pure culture of bacteria.

The bacterial extract can be obtained as follows. The bacteria of choice are grown up overnight in any of a number of growth media and under growth conditions that are well known in the art and easily optimized by a practitioner for growth of the particular bacteria. For example, strains of *E.*

*coli* can be conveniently be grown in nutrient medium, brain heart infusion medium, yeast extract/tryptone medium, and the like, at an incubation temperature of about 37° C., with or without agitation. Cells are harvested from the overnight culture by low speed centrifugation or filtration, and the cells can be lysed by suspending the cell pellet in a suitable cell suspension buffer, and disrupting the suspended cells by sonication or breaking the suspended cells in a French press. The cell lysate is centrifuged or filtered to remove large contaminating DNA fragments. The supernatant or filtrate recovered can be combined with a pre-incubation mixture comprising some or all of the components needed for transcription and/or translation of a template nucleic acid, such as pyruvate kinase, $Mg^{2+}$, GTP, ATP, PEP, a reducing agent, such as dithiothreitol, and amino acids, dialyzed and centrifuged to remove contaminating membranes, and then stored before use. In a preferred embodiment, the bacterial extract is prepared as described in Example 1 below.

2. Preparation of Nucleic Acid Template

Both DNA and RNA encoding the desired protein are suitable for use in the methods of the invention. DNA template and RNA template for use in the methods of the invention can be constructed as follows.

a. DNA Template

A DNA template that functions in the methods of the invention can be constructed by operably linking a desired protein-encoding DNA to both a promoter sequence and a bacterial ribosome binding site (Shine-Dalgarno sequence). Promoters suitable for use with DNA template in the cell-free transcription-translation methods of the invention include any DNA sequence capable of promoting transcription in vivo in the bacteria from which the bacterial extract is derived. Preferred are promoters that are capable of efficient, i. e., strong, initiation of transcription in vivo in the bacteria used to prepare the bacterial extract. Strong bacterial promoters include the β-lactamase and lactose promoter systems (Chang et al., *Nature,* 275: 615 (1978); and Goeddel et al., *Nature,* 281: 544 (1979)), alkaline phosphatase, a tryptophan (trp) promoter system (Goeddel, *Nucleic Acids Res.,* 8: 4057 (1980) and EP 36,776) and hybrid promoters such as the tac promoter (deBoer et al., *Proc. Natl. Acad. Sci. USA,* 8: 21–25 (1983)). However, other known bacterial promoters are suitable, such as T7 promoter systems (Studier et al., *Meth. Enzymol.,* 185: 60–89 (1990)), as are SP6 promoters and other viral promoters.

DNA encoding the desired protein and DNA containing the desired promoter and Shine-Dalgamo (SD) sequences can be prepared by a variety of methods known in the art. These methods include, but are not limited to, chemical synthesis by any of the methods described in Engels et al., *Agnew. Chem. Int. Ed. Engl.,* 28: 716–734 (1989), the entire disclosure of which is incorporated herein by reference, such as the triester, phosphite, phosphoramidite and H-phosphonate methods. In one embodiment, codons preferred by the bacteria from which the bacterial extract is derived are used in the design of the desired protein-encoding DNA. Alternatively, the desired DNA sequences can be obtained from existing clones or, if none are available, by screening DNA libraries and constructing the desired DNA sequences from the library clones.

Once the desired protein-encoding, promoter and SD sequences have been obtained, a DNA template can be constructed by operably ligating the sequences together using linkers or adaptors to supply any required restriction sites according to methods known in the art (Siebenlist et al., *Cell,* 20: 269 (1980)) such that the RNA polymerase present in the reaction mixture is able to bind to and transcribe the DNA template and such that the ribosomes present in the reaction mixture are able to bind and translate RNA transcripts of the DNA template. Suitable quantities of DNA template for use herein can be produced by amplifying the DNA in well known cloning vectors and hosts, such as plasmid vectors carrying the pBR322 origin of replication for autonomous replication in most Gram-negative bacterial hosts, plasmid vectors carrying the pC194 (Ehrlich, *Proc. Natl. Acad. Sci. USA,* 75: 1433–1436 (1978)) origin of replication for autonomous replication in Bacillus and some other Gram-positive bacterial hosts, or 2-micron circle (21plasmid) vectors carrying an origin of replication for autonomous replication in most yeast hosts.

Alternatively, the DNA template can be amplified by polymerase chain reaction (PCR) as described by Saiki et al., Science, 230: 1350 (1985), Mullis et al, *Cold Spring Harbor Symp. Quant. Biol.,* 51: 263 (1986), Mullis and Faloona, *Methods Enzymol.,* 155: 335 (1987), and Saiki et al., Science, 239: 487 (1988).

b. RNA Template

For embodiments using RNA template, RNA encoding the protein of interest can be conveniently produced from a recombinant host cell transformed with a vector constructed to express a mRNA with a bacterial ribosome binding site (SD sequence) operably linked to the coding sequence of the desired gene such that the ribosomes in the reaction mixture are capable of binding to and translating such mRNA. Thus, the vector carries any promoter capable of promoting the transcription of DNA in the particular host cell used for RNA template synthesis.

Since it is difficult to extract undegraded RNA from bacteria, higher eukaryotic cell culture is preferred for the production of RNA template. In principle, any higher eukaryotic cell culture is workable, including both vertebrate and invertebrate cell cultures. For example, RNA template can be produced in dicotyledonous plant cell cultures transformed with vectors derived from the Ti plasmid of *Agrobacterium tumefaciens,* in insect cell cultures transformed with baculovirus-derived vectors, avian cell cultures transformed with fowlpox-derived vectors, or mammalian cell cultures transformed with simian virus-40 (SV-40)-derived vectors.

The RNA template can be conveniently isolated in a total cellular RNA fraction extracted from the host cell culture. Total cellular RNA can be isolated from the host cell culture by any method known in the art such as, in the case of RNA template produced in mammalian host cells, the methods described by Favaloro et al., *Methods Enzymol.,* 65: 718 (1980), Stallcup and Washington, *J. Biol. Chem.,* 258: 2802 (1983), Birnboim, *Nucleic Acids Res.,* 16: 1487 (1988), Gilsin et al, *Biochemistry,* 13: 2633 (1974), Ullrich et al., Science, 196: 1313 (1977), Strohman et al., *Cell,* 10: 265 (1977), and MacDonald et al., *Methods Enzymol.,* 152: 219 (1987).

In a preferred embodiment, a mRNA fraction isolated from total cellular RNA is used as the template in the cell-free translation methods of the invention. The desired RNA template can be isolated along with most of the cellular mRNA if the RNA template is designed to contain at its 3' terminus a polyadenylation signal recognized by the eukaryotic host cell. Thus, the host cell will produce the RNA template with a polyadenylate (poly(A)) tail. Polyadenylated mRNAs can be separated from the bulk of cellular RNA by affinity chromatography on oligodeoxythymidylate (oligo (dT))-cellulosecolumns using any method known in the art, such as the method of Edmonds et al., *Proc. Natl. Acad. Sci.,* 68: 1336 (1971) or the method of Aviv and Leder, Proc. Natl. Acad. Sci., 69: 1408 (1972).

If the size of the mRNA encoding the desired protein is known, the mRNA preparation can be further purified for mRNA molecules of the particular size by agarose gel electrophoresis of RNA in the presence of methylmercuric hydroxide as described in Lemischka et al., *J. Mol. Biol.*, 151: 101 (1981) or fractionation of RNA by sucrose density gradient centrifugation in the presence of methylmercuric hydroxide as described by Schweinfest et al, *Proc. Natl. Acad. Sci.*, 79: 4997 (1982).

3. Procedures for Conducting In Vitro Protein Synthesis Reactions

The invention encompasses any method of in vitro protein synthesis wherein a nucleic acid encoding a desired protein is expressed in a reaction mixture comprising a bacterial-cell free extract and a reducing agent (or agents) and wherein the concentration of dissolved oxygen ($DO_2$) is regulated such that complete oxidation of the reducing agent concentration does not occur for a selected period of time following initiation of protein synthesis in the reaction mixture. Accordingly, the invention can be practiced by obtaining a nucleic acid encoding the desired protein as described above, obtaining a bacterial extract as described above and combining the nucleic acid with the bacterial extract and a reducing agent or agents to form a reaction mixture wherein a reducing environment is maintained by regulating the $DO_2$ concentration in the reaction mixture by any of the methods described above. The desired reducing agent concentration in the reaction mixture can be achieved by admixing the reducing agent (or agents) to the bacterial extract and/or nucleic acid components prior to formation of the reaction mixture, or by using a bacterial extract preparation that contains the reducing agent (or agents), or by admixing the reducing agent (or agents) to the reaction mixture concomitantly with the bacterial extract and nucleic acid components, or any combination thereof. In a preferred embodiment, the bacterial extract is prepared with a reducing agent (or agents) as described above in order to protect against oxidative inactivation of protein synthesis enzymes prior to use. In some embodiments, the protein synthesis capability of the bacterial extract is enhanced by the addition of any component or combination of components, including amino acids, NTPs, PEP, pyruvate kinase, 3',5'-cAMP, tRNAs, transcription and/or translation initiation factors, polyols, magnesium salts, etc., that facilitates in vitro transcription and/or translation in the reaction mixture.

In embodiments of the invention wherein DNA template is used to drive in vitro protein synthesis, the individual components of the in vitro transcription-translation mixture can be admixed together in any convenient order. It will be appreciated that the order of admixing is not important to the invention. In a preferred embodiment, some components for feeding transcription and translation, e. g., ATP, CTP, GTP, UTP, PEP, a reducing agent (if needed in addition to or in place of the reducing agent concentration supplied by the bacterial extract preparation), all amino acids except methionine, 3',5'-cAMP, and tRNAs, etc., along with initiation factors such as folinic acid, $NADP^+$, FAD, pyridoxine hydrochloride (HCl), PABA, folic acid, and a suitable polyol, such as PEG-6000, are combined with DNA, magnesium acetate or other magnesium salt, radiolabeled and/or unlabeled methionine, and buffer to form a DNA premix.

Optionally, an RNA polymerase is added to the DNA premix to provide enhanced transcription of the DNA template. RNA polymerases suitable for use herein include any RNA polymerase that functions in the bacteria from which the bacterial extract is derived. In the case of an *E. coli*-derived bacterial extract, an *E. coli* RNA polymerase or a viral RNA polymerase from any bacteriophage that infects *E. coli*, such as T7 RNA polymerase, will enhance transcription in the methods of the invention.

The DNA premix can then be combined with bacterial extract to form the reaction mixture, and placed under a non-oxygen or limited oxygen atmosphere in the reaction vessel or placed in a reaction vessel with no headspace as described above. In a particularly preferred embodiment, the reaction components are admixed and the reactions are conducted as described in Example 2 below.

In embodiments of the invention that use RNA template to drive in vitro protein synthesis, the components of the reaction mixture can be admixed together in any convenient order, but are preferably admixed in an order wherein the RNA template is added last. In a preferred embodiment, some components for feeding translation, e.g., ATP, GTP, all amino acids except methionine, tRNAs, etc., along with initiation factors such as folinic acid, $NADP^+$, FAD, pyridoxine HCl, PABA, folic acid, and a suitable polyol, such as PEG-6000, and a reducing agent (if needed in addition to or in place of the reducing agent concentration provided by the bacterial extract preparation), are combined with the bacterial extract and magnesium acetate or other magnesium salt. This mixture can then be combined with RNA, radiolabeled and/or unlabeled methionine and buffer to form the reaction mixture, and placed under a non-oxygen or limited oxygen atmosphere in the reaction vessel or placed in a reaction vessel with no head space as described above.

The reaction mixture can be incubated at any temperature suitable for the transcription and/or translation reactions, such temperature usually being the optimal growth temperature of the bacteria from which the bacterial extract is derived, i.e., the temperature at which the bacterial protein synthesis machinery operates with highest efficiency. In embodiments that use a bacterial extract derived from a mesophilic strain of *E coli*, the incubation temperature is preferably from about 20° C. to about 42° C., and more preferably about 37° C.

The reaction mixture can be agitated or unagitated, as desired, during incubation. The use of agitation enhances the speed and efficiency of protein synthesis by keeping the concentrations of reaction components uniform throughout the reaction vessel and avoiding the formation of pockets with low rates of synthesis caused by the depletion of one or more key components. However, agitation will also facilitate the gas/liquid transfer of any $O_2$ present in the reaction vessel headspace, thereby increasing $DO_2$ in the reaction mixture and eventually lowering the synthetic rate and/or yield of protein. Typically, the improved reaction kinetics provided by agitation will outweigh any detriment caused by the increased $DO_2$ level if the headspace atmospheric oxygen content is not sufficient to increase the $DO_2$ level by more than about 0.75 mM upon complete transfer of the atmospheric oxygen to liquid phase in the reaction mixture. In embodiments wherein the reaction is conducted under a non-oxygen atmosphere or in a vessel with no headspace, agitation is preferred because such systems have no gas/liquid transfer of $O_2$.

The reaction can be allowed to continue while protein synthesis occurs at an acceptable specific or volumetric rate, or until cessation of protein synthesis, as desired. The reaction can be conveniently stopped by incubating the reaction mixture on ice. In one embodiment, the reaction is maintained as long as desired by continuous feeding of the limiting and non-reusable transcription and translation components into the reaction vessel, including continuous feeding of a reducing agent (or agents) to avoid dilution of the reducing agent (or agents) concentration in the reaction mixture, optionally coupled with continuous removal of the desired protein from the reaction vessel. For example, the invention includes embodiments that incorporate the continuous flow in vitro transcription-translation system described by Baranov et al. (1989), supra. In a particularly preferred RNA template-driven method, the RNA template is continuously fed into the reaction vessel to offset any degradation of RNA template caused by contaminating RNases. It is preferable to control the $DO_2$ concentration in the feed vessel in order to limit the oxidation of reducing agent that occurs in the feed solution before it is added to the reaction mixture.

Upon cessation of in vitro protein synthesis, the desired protein is optionally recovered from the reaction mixture by any isolation or purification procedure needed for detecting, analyzing or harvesting the desired protein.

The methods of the invention encompass the use of all ranges of reaction component concentrations that provide an acceptable rate of in vitro protein synthesis. It will be appreciated that the use of a reaction mixture comprising a reducing agent or agents wherein the $DO_2$ level is regulated or limited such that the reducing environment is maintained (i.e. complete oxidation of the reducing agent concentration is not allowed to occur) will increase the duration of protein synthesis in any cell-free bacterial extract system of in vitro protein synthesis. Nevertheless, certain ranges of component concentrations are preferable for the maximization of the rate and yield of protein synthesis.

In the final reaction mixture, the DNA template can be present at a concentration of about 0.02 to about 3 mg/ml. Preferably, the DNA template concentration in the reaction mixture is from about 0.05 mg/ml to about 1.2 mg/ml, and more preferably about 0.28 mg/ml to about 1.2 mg/ml, and still more preferably about 0.83 mg/ml to about 1.2 mg/ml, and most preferably about 1.2 mg/ml.

If an RNA template is used, the RNA template can be present in the final reaction mixture in a concentration of about 0.02 to about 5 mg/ml, and preferably about 0.5 to about 2 mg/ml, and more preferably about 1 to about 2 mg/ml.

The invention encompasses the use of any concentration of bacterial extract that is effective in the in vitro transcription and/or translation methods described herein. A bacterial cytoplasmic protein concentration of about 5 mg/ml to about 120 mg/ml in the reaction mixture is suitable for use in the methods of the invention. In the case of DNA template driven reactions, the preferred bacterial extract concentration will depend upon whether a maximized specific rate or a maximized volumetric rate of protein synthesis is desired. A maximized specific rate of protein synthesis is achieved with a bacterial cytoplasmic protein concentration of about 10 to about 15 mg/ml. In order to maximize the volumetric rate of protein synthesis with respect to bacterial extract concentration, a bacterial extract concentration is selected for maximum performance at the particular DNA concentration to be used. For example, at a DNA concentration of about 0.05 mg/ml, the effective range of bacterial cytoplasmic protein concentration is about 5 mg/ml to about 20 mg/ml. At a DNA concentration of about 0.30 mg/ml, the effective range of bacterial cytoplasmic protein concentration is from about 5 mg/ml to about 30 mg/ml. At a DNA concentration of about 1.0 mg/ml, the effective range of bacterial cytoplasmic protein concentration is from about 5 mg/ml to about 80 mg/ml, and preferably about 50 mg/ml to about 60 mg/ml as shown in Example 3 below.

Any source of magnesium dication can be used in the cell-free protein synthesis methods of the invention. Preferably, a magnesium salt, such as magnesium acetate, magnesium chloride, magnesium phosphate, etc., is used. Magnesium dication concentrations suitable for use herein are in the range of about 5 to 15 mM.

In a preferred embodiment, a polyol is used to stabilize proteins in the reaction mixture. In a more preferred embodiment, a polyether is used in the reaction mixture. Particularly preferred polyethers for use herein are polyethylene glycols (PEGs) of about 200 to about 35,000 daltons (D) in average molecular weight, and most preferred is a PEG with an average molecular weight of 6,000 D (PEG-6000). The use of polyethylene glycols to stabilize proteins is reviewed in *Pharm. Res.*, 8: 285–291 (1991). In the final reaction mixture, a polyol can be present in a concentration of about 0.1% weight to volume (w/v) to about 30% (w/v). Preferably, a polyol concentration of about 1% (w/v) to about 5% (w/v) is used.

Various combinations and concentrations of initiation factors can be used in the cell-free protein synthesis methods of the invention. Such initiation factors include 3',5'-cAMP, folinic acid, pyridoxine HCl, PABA, $NADP^+$, FAD, and folic acid. For example, the invention encompasses the use of a reaction mixture that contains 3',5'-cAMP at a concentration of about 0.05 mM to about 1.0 mM, and preferably about 0.2 mM to about 0.4 mM, folinic acid at a concentration of about 10 μg/ml to about 35 μg/ml, and preferably about 15 μg/ml to about 20 μg/ml, pyridoxine HCl at a concentration of about 20 μg/ml to about 35 μg/ml, and preferably about 25 μg/ml to about 30 μg/ml, PABA at a concentration of about 8 μg/ml to about 15 μg/ml, and preferably about 10 μg/ml to about 12 μg/ml, NADP+ at a concentration of about 20 μg/ml to about 35 μg/ml, and preferably about 25 μg/ml to about 30 μg/ml, FAD at a concentration of about 20 μg/ml to about 35 μg/ml, and preferably about 25 μg/ml to about 30 μg/ml, and/or folic acid at a concentration of about 20 μg/ml to about 35 μg/ml, and preferably about 25 μg/ml to about 30 μg/ml.

In embodiments using DNA template to drive in vitro transcription/translation, some components of the transcription and/or translation system in the bacterial extract can be advantageously supplemented to increase the availability of such components in the reaction mixture. In a preferred embodiment, the reaction mixture contains one or more of the following: (1) an initial concentration of GTP, UTP and CTP of about 0.5 mM to about 2.0 mM, and preferably about 0.85 mM; (2) an initial concentration of ATP of about 0.5 mM to about 2.5 mM, and preferably about 1.22 mM; (3) an initial concentration of PEP of about 10 mM to about 50 mM, and preferably about 27.0 mM; (4) a concentration of pyruvate kinase of about 0.05 units/ml to about 0.5 units/ml, and preferably about 0.2 units/ml; (5) an initial concentration of tRNAs of about 0.05 mg/ml to about 0.3 mg/ml, and preferably about 0.17 mg/ml; (6) an initial concentration of all 19 amino acids (all amino acids except methionine) of about 0.2 mM to about 0.6 mM, and preferably about 0.35 mM; and (7) an initial concentration of methionine of about 0.6 micromoles/liter (μM) to about 2.0 mM, and preferably about 4.3 μM to about 2.0 mM, and more preferably about 0.1 mM to about 2.0 mM, and most preferably about 1.0 mM to about 2.0 mM.

In embodiments using RNA template to drive in vitro translation, some components of the translation system in the bacterial extract can be advantageously supplemented to increase the availability of such components in the reaction mixture. In a preferred embodiment, the reaction mixture contains one or more of the following: (1) an initial concentration of GTP of about 0.5 mM to about 2.0 mM, and preferably about 0.85 mM; (2) an initial concentration of ATP of about 0.5 mM to about 2.5 mM, and preferably about 1.22 mM; (3) an initial concentration of PEP of about 10 mM to about 50 mM, and preferably about 27.0 mM; (4) a concentration of pyruvate kinase of about 0.05 units/ml to about 0.5 units/ml, and preferably about 0.2 units/ml; (5) an initial concentration of tRNAs of about 0.05 mg/ml to about 0.3 mg/ml, and preferably about 0.17 mg/ml; (6) an initial concentration of all 19 amino acids (all amino acids except methionine) of about 0.2 mM to about 0.6 mM, and preferably about 0.35 mM; and (7) an initial concentration of methionine of about 0.6 micromoles/liter($\mu$M) to about 2.0 mM, and preferably about 4.3 $\mu$M to about 2.0 mM, and more preferably about 0.1 mM to about 2.0 mM, and most preferably about 1.0 mM to about 2.0 mM.

The invention also encompasses the use of labeled and/or unlabeled methionine in cell-free protein synthesis methods. The incorporation of labeled methionine in the desired protein is useful for detection of the protein product by any of a number of techniques well known in the art. Radiolabeled methionine, such as $^{35}$S- or $^{14}$C-labeled methionine, is particularly useful herein. In one embodiment, the radiolabeled methionine represents only a fraction of the total methionine used in the reaction mixture in order to avoid using excess radioactivity. Alternatively, other radiolabeled amino acids, such as $^3$H-labeled leucine, can be used.

The concentration of reactants and the volume of the reaction mixture can be adjusted by addition of a suitable buffer. Suitable buffers for use herein include any diluent that provides a chemical environment in which the cell-free protein synthesis machinery is capable of operating efficiently, e.g., an environment that approximates the ionic strength, pH, etc., in the cytoplasm of the particular bacterium from which the bacterial extract is derived. Thus, the buffer is chosen according to the requirements of the particular bacterial extract used in the in vitro protein synthesis method. Although the methods of the invention can be practiced using buffers containing calcium salts, superior performance can be obtained by excluding calcium salts from the buffer, particularly in embodiments utilizing higher concentrations of bacterial extract. In methods using *E coli*-derived extracts, preferred buffers include a Tris (hydroxymethyl)aminomethane-acetate (TAE) buffer with or without other non-calcium salts such as ammonium acetate or potassium acetate.

It is desirable to minimize RNase degradation of RNAs encoding the desired protein in practicing the in vitro transcription and/or translation methods of the invention. Thus, in some preferred embodiments, essentially RNase free conditions are maintained throughout the procedures described herein. Suitable inhibitors of RNase activity, such as diethylpyrocarbonate (DEPC), can be used to treat the reaction vessel and all glassware, centrifuge tubes, plastic tubing or other equipment by filling (or soaking) the apparatus for 1 hour in distilled water to which DEPC (1 ml DEPC/liter of water) has been added just before use. Also, all stock solutions can be made with DEPC-treated distilled water. In addition, RNA degradation caused by RNases present in the bacterial extract can be reduced by preparing the extract from a bacterial strain known to lack major RNase activity, such as *E. coli* strain MRE600 (Pratt, J. M., "Coupled Transcription-Translation in Prokaryotic Cell-Free Systems", in Transcription and Translation: A Practical Approach, Hames and Higgins, eds, IRL Press (1987), pp.179–209), and by adding an RNase inhibitor to the in vitro transcription-translation reaction mixture.

II. Compositions for Optimized Cell-Free Protein Synthesis with Regulated $DO_2$ In addition to the methods of cell-free protein synthesis which regulate $DO_2$ concentration as described in Section I above, the invention also encompasses the compositions used in such methods of cell-free protein synthesis. Thus, the invention provides a composition comprising a reaction mixture comprising a bacterial cell-free extract, $DO_2$, a reducing agent or agents, and a nucleic acid encoding a desired protein, wherein the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture. The composition of the invention can be made by obtaining a bacterial extract, obtaining a nucleic acid encoding the desired protein, combining the bacterial extract and the nucleic acid to form a reaction mixture, wherein the desired reducing agent concentration is supplied by pre-admixing the bacterial extract or other reaction mixture component(s) with the reducing agent (or agents), or by admixing the reducing agent to the reaction mixture concomitantly with the other reaction mixture components, or any combination thereof, and regulating the $DO_2$ concentration in the reaction mixture by any of the methods described in Section I above. For example, the compositions of the invention can be created by maintaining such reaction mixtures in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g., argon, or in a reaction vessel with no headspace as described in Section I above.

In a preferred embodiment, the composition comprises an additional component or combination of components in the reaction mixture, and/or an enhanced concentration of a component or combination of components in the reaction mixture, which improves the reaction mixture's in vitro transcription and/or translation capabilities. Suitable types and concentrations of such components are described in Section I(3) above, and can be obtained and incorporated into the compositions of the invention by any of the methods described in Section I(3) above.

In a particularly preferred embodiment, the composition of the invention further comprises a desired protein-encoding DNA at a concentration of about 0.05 mg/ml to about 1.2 mg/ml, a bacterial cell-free extract derived from a pure culture of an *E. coli* bacterium, a reducing agent that is dithiothreitol and is present at a concentration of about 1.3 mM to about 1.8 mM, and a polyethylene glycol with an average molecular weight of about 6,000 D (PEG-6000) at a concentration of about 1 percent (w/v) to about 5 percent (w/v), and the composition is under an argon atmosphere.

III. Optimized Cell-Free Protein Synthesis with High [Met]

The invention also provides methods for increasing the specific rate or volumetric rate of in vitro protein synthesis by using an initial methionine concentration of at least about 0.1 mM, or at least about 0.3 mM, or at least about 0.5 mM, or at least about 1.0 mM, or at least about 1.5 mM, or at least about 1.75 mM, or at least about 2.0 mM. Accordingly, the invention encompasses any method of in vitro protein synthesis wherein a nucleic acid encoding a desired protein is expressed in a reaction mixture comprising a bacterial cell-free extract and an initial methionine concentration of at least about 0.1 mM, or at least about 0.3 mM, or at least about 0.5 mM, or at least about 1.0 mM, or at least about 1.5 mM, or at least about 1.75 mM, or at least about 2.0 mM. In another embodiment, the invention provides a method of in vitro protein synthesis wherein a nucleic acid encoding a desired protein is expressed in a reaction mixture comprising a bacterial cell-free extract and an initial methionine concentration of about 0.1 mM to about 2.0 mM, or about 0.3 mM to about 2.0 mM, or about 0.5 mM to about 2.0 mM, or about 1.0 mM to about 2.0 mM, or about 0.1 mM to about 1.75 mM, or about 0.3 mM to about 1.75 mM, or about 0.5 mM to about 1.75 mM, or about 1.0 mM to about 1.75 mM.

Optionally, the desired protein can be recovered from the reaction mixture.

These embodiments of the invention are conveniently practiced by boosting the initial methionine concentration used in any of the methods of cell-free protein synthesis described in Section I(3) above, with or without the procedures for regulating the $DO_2$ concentration in the reaction mixture described in Section I above. The higher methionine concentrations described herein can be conveniently attained by supplementing one of the reaction mixture components, such as the bacterial extract, with methionine prior to use in the reaction mixture, or by concomitantly admixing the methionine to the other components at the time the reaction mixture is formed, or by any combination thereof. In addition to the examples described herein, it will be appreciated that the methods and compositions of the invention can be practiced using any protocol that achieves the initial methionine concentrations provided herein.

As discussed above, the methods of the invention encompass the use of labeled methionine, such as $^{35}S$ or $^{14}C$ radiolabeled methionine, and/or unlabeled methionine. Accordingly, the initial methionine concentration in the reaction mixture can be increased with labeled methionine, such as $^{35}S$ or $^{14}C$ radiolabeled methionine, unlabeled methionine, or a combination of labeled and unlabeled methionine. To avoid adding excess radioactivity, the methionine concentration can be made up of a mixture of radiolabeled and unlabeled methionine wherein the radiolabeled methionine represents only a fraction of the total methionine used in the reaction mixture. Thus, the invention provides a method of in vitro protein synthesis comprising expressing a nucleic acid encoding a desired protein in a reaction mixture comprising a bacterial extract, labeled methionine, and unlabeled methionine, wherein the initial concentration of unlabeled methionine is at least about 0.1 mM. In another embodiment, the reaction mixture contains both labeled and unlabeled methionine, and the initial concentration of unlabeled methionine is at least about 0.3 mM, or at least about 0.5 mM, or at least about 1.0 mM, or at least about 1.5 mM, or at least about 1.75 mM, or at least about 2.0 mM. In yet another embodiment, the reaction mixture contains both labeled and unlabeled methionine, and the initial concentration of unlabeled methionine is about 0.1 mM to about 2.0 mM, or about 0.3 to about 2.0 mM, or about 0.5 mM to about 2.0 mM, or about 1.0 mM to about 2.0 mM. In still another embodiment, the reaction mixture contains both labeled and unlabeled methionine, and the initial concentration of unlabeled methionine is about 0.1 mM to about 1.75 mM, or about 0.3 mM to about 1.75 mM, or about 0.5 mM to about 1.75 mM, or about 1.0 mM to about 1.75 mM.

In a further embodiment, the invention provides a method for cell-free protein synthesis comprising expressing a nucleic acid in a reaction mixture comprising a bacterial extract and either labeled or unlabeled methionine, or a combination thereof, wherein the labeled methionine, unlabeled methionine, or combination thereof provides an initial methionine concentration of at least about 1.0 mM. In a preferred embodiment, the labeled methionine, unlabeled methionine, or combination thereof provides an initial methionine concentration of at least about 1.5 mM, or at least about 1.75 mM, or at least about 2.0 mM. In another preferred embodiment, the labeled methionine, unlabeled methionine, or combination thereof provides an initial methionine concentration of about 1.0 mM to about 2.0 mM, or about 1.0 mM to about 1.75 mM.

In a preferred embodiment, the reaction mixture comprises an additional component or combination of components, and/or an enhanced concentration of a component or combination of components, which improves the reaction mixture's in vitro transcription and/or translation capabilities. Suitable types and concentrations of such components are set forth in Section I(3) above, and can be obtained and used as described therein.

In a more preferred embodiment, the reaction mixture comprises unlabeled methionine and labeled methionine, a desired protein-encoding DNA at a concentration of at least about 0.05 mg/ml, and a PEG at a concentration of about 1% (w/v) to about 5%(w/v), wherein the PEG is about 200 D to 35,000 D in average molecular weight, and preferably is PEG-6000, and wherein the unlabeled methionine is present at an initial concentration of about 0.1 mM to about 2.0 mM.

In an even more preferred embodiment, the reaction mixture comprises labeled methionine and unlabeled methionine, a desired protein-encoding DNA at a concentration of at least about 1.2 mg/ml, a PEG-6000 concentration of at least about 5%(w/v), wherein the unlabeled methionine is present at an initial concentration of about 0.1 mM to about 2.0 mM.

In a still more preferred embodiment, the reaction mixture comprises (in addition to higher initial concentrations of unlabeled methionine and a higher concentration of DNA template and PEG) an initiation factor cocktail including one or more of the following: an initial concentration of $NADP^+$ of at least about 27 $\mu$g/ml, an initial concentration of FAD of at least about 27 $\mu$g/ml, an initial concentration of pyridoxine hydrochloride (HCl) of at least about 27 $\mu$g/ml, an initial concentration of PABA of at least about 11 $\mu$g/ml, an initial concentration of 3',5'-cAMP of at least about 0.34 mM, an initial concentration of folinic acid of at least about 18 $\mu$g/ml, an initial concentration of folic acid of at least about 27 $\mu$g/ml, initial concentrations of GTP, UTP, and CTP of at least about 0.85 mM, an initial concentration of ATP of at least about 1.22 mM, an initial concentration of PEP of at least about 27 mM, an initial concentration of pyruvate kinase of at least about 0.2 units/ml, initial concentrations of tRNAs of at least about 0.17 mg/ml, and initial concentrations of all amino acids (except methionine) of at least about 0.35 mM.

Also provided herein are methods for cell-free protein synthesis in which both the rates and duration of protein synthesis are enhanced by boosting the methionine concentration in the reaction mixture according any of the methods described above and by maintaining a reducing environment in the reaction mixture according to any of the methods described in Section I above. Thus, the invention encompasses methods for in vitro protein synthesis comprising expressing a nucleic acid encoding a desired protein in a reaction mixture comprising a bacterial cell-free extract, a reducing agent (or agents), $DO_2$ and methionine, wherein the methionine is present at an initial concentration of at least about 0.1 mM, or at least about 0.3 mM, or at least about 0.5 mM, or at least about 1.0 mM, or at least about 1.5 mM, or at least about 1.75 mM, or at least about 2.0 mM, and the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture. For example, reaction mixtures with such high methionine concentrations can be maintained in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g., argon, or in a reaction vessel with no headspace as described in Section I above.

The invention additionally encompasses methods for in vitro protein synthesis comprising expressing a nucleic acid encoding a desired protein in a reaction mixture comprising a bacterial cell-free free extract, a reducing agent (or agents), $DO_2$, and methionine, wherein the methionine is present at an initial concentration of about 0.1 mM to about 2.0 mM, or about 0.3 mM to about 2.0 mM, or about 0.5 mM to about 2.0 mM, or about 1.0 mM to about 2.0 mM, or about 0.1 mM to about 1.75 mM, or about 0.3 mM to about 1.75 mM, or about 0.5 mM to about 1.75 mM, or about 1.0 mM to about 1.75 mM, and the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture. For example, reaction mixtures with such high methionine concentrations can be maintained in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g., argon, or in a reaction vessel with no headspace as described in Section I above.

In another embodiment, the reaction mixture contains both labeled and unlabeled methionine, a reducing agent (or agents), and $DO_2$, wherein the initial concentration of unlabeled methionine is at least about 0.1 mM, or at least about 0.3 mM, or at least about 0.5 mM, or at least about 1.0 mM, or at least about 1.5 mM, or at least about 1.75 mM, or at least about 2.0 mM, and wherein the $DO_2$ concentration is regulated such that complete oxidation of the reducing agent concentration does not occur for a period of at least about 30 minutes, or at least about 40 minutes, or at least about one hour, or at least about 2 hours, following initiation of protein synthesis in the reaction mixture. In such embodiments, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g., argon, or by maintaining the reaction mixture in a reaction vessel that contains no headspace as described in Section I above.

In yet another embodiment, the reaction mixture contains both labeled and unlabeled methionine, a reducing agent (or agents), and $DO_2$, wherein the initial concentration of unlabeled methionine is about 0.1 mM to about 2.0 mM, or about 0.3 to about 2.0 mM, or about 0.5 mM to about 2.0 mM, or about 1.0 mM to about 2.0 mM, or about 0.1 mM to about 1.75 mM, or about 0.3 mM to about 1.75 mM, or about 0.5 mM to about 1.75 mM, or about 1.0 mM to about 1.75 mM, and wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such embodiments, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

In a further embodiment, the invention provides a method for cell-free protein synthesis comprising expressing a nucleic acid in a reaction mixture comprising a bacterial extract and either labeled or unlabeled methionine, or a combination thereof, a reducing agent, and $DO_2$, wherein the labeled methionine, unlabeled methionine, or combination thereof provides an initial methionine concentration of at least about 1.0 mM, or at least about 1.5 mM, or at least about 1.75 mM, or at least about 2.0 mM, and wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such embodiments, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

In yet another embodiment, the invention provides a method for cell-free protein synthesis comprising expressing a nucleic acid in a reaction mixture comprising a bacterial extract and either labeled or unlabeled methionine, or a combination thereof, a reducing agent, and $DO_2$, wherein the labeled methionine, unlabeled methionine, or combination thereof provides an initial methionine concentration of about 1.0 mM to about 2.0 mM, or about 1.0 mM to about 1.75 mM, and wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such embodiments, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

IV. Compositions for Optimized Cell-Free Protein Synthesis with High (Met)

In addition to the methods of cell-free protein synthesis using an increased initial methionine concentration described in Section III above, the invention also encompasses the compositions used in such methods of cell-free protein synthesis. Thus, the invention provides a composition comprising a reaction mixture comprising a bacterial cell-free extract, a nucleic acid encoding a desired protein, and methionine, wherein the methionine is present at an initial concentration of at least about 0.1 mM, or at least about 0.3 mM, or at least about 0.5 mM, or at least about 1.0 mM, or at least about 1.5 mM, or at least about 1.75 mM, or at least about 2.0 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

Also encompassed herein is a composition comprising a reaction mixture comprising a bacterial cell-free extract, a nucleic acid encoding a desired protein, and methionine, wherein the methionine is present at an initial concentration of about 0.1 mM to about 2.0 mM, or about 0.3 mM to about 2.0 mM, or about 0.5 mM to about 2.0 mM, or about 1.0 mM to about 2.0 mM, or about 0.1 mM to about 1.75 mM, or about 0.3 mM to about 1.75 mM, or about 0.5 MM to about 1.75 mM, or about 1.0 mM to about 1.75 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

In another embodiment, the invention provides a composition comprising a reaction mixture comprising a bacterial cell-free extract, a nucleic acid encoding a desired protein, labeled methionine, and unlabeled methionine, wherein the unlabeled methionine is present at an initial concentration of at least about 0.1 mM, or at least about 0.3 mM, or at least about 0.5 mM, or at least about 1.0 mM, or at least about 1.5 mM, or at least about 1.75 mM, or at least about 2.0 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

The invention further provides a composition comprising a reaction mixture comprising a bacterial cell-free extract, a nucleic acid encoding a desired protein, labeled methionine, and unlabeled methionine, wherein the unlabeled methionine is present at an initial concentration of about 0.1 mM to about 2.0 mM, or about 0.3 mM to about 2.0 mM, or about 0.5 mM to about 2.0 mM, or about 1.0 mM to about 2.0 mM, or about 0.1 mM to about 1.75 mM, or about 0.3 mM to about 1.75 mM, or about 0.5 mM to about 1.75 mM, or about 1.0 mM to about 1.75 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

In yet another embodiment, the composition comprises a reaction mixture comprising a bacterial cell-free extract, a nucleic acid encoding a desired protein, and either labeled methionine or unlabeled methionine, or a combination thereof, wherein the labeled methionine, unlabeled methionine, or combination thereof provides an initial methionine concentration of at least about 1.0 mM, or at least about 1.5 mM, or at least about 1.75 mM, or at least about 2.0 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g. argon, or by maintaining the reaction mixture in a reaction vessel that contains no headspace as described in Section I above.

In still another embodiment, the composition comprises a reaction mixture comprising a bacterial cell-free extract, a nucleic acid encoding a desired protein, and either labeled methionine or unlabeled methionine, or a combination thereof, wherein the labeled methionine, unlabeled methionine, or combination thereof provides an initial methionine concentration of about 1.0 mM to about 2.0 mM, or at about 1.0 mM to about 1.75 mM. Optionally, the composition further comprises a reducing agent (or agents) and $DO_2$, wherein the $DO_2$ concentration is regulated such that complete oxidation of the reducing agent concentration does not occur for a period of at least about 30 minutes, or at least about 40 minutes, or at least about one hour, or at least about 2 hours, following the initiation of protein synthesis in the reaction mixture. In such compositions, the $DO_2$ concentration can be conveniently regulated, for example, by maintaining the reaction mixture in a reaction vessel under conditions wherein the transfer of oxygen from the atmosphere occupying the reaction vessel headspace to liquid phase in the reaction mixture is limited, e.g., by maintaining the reaction mixture under a limited oxygen atmosphere, such as an atmosphere that cannot increase the $DO_2$ concentration by more than about 0.75 mM upon complete transfer of atmospheric oxygen to liquid phase in the reaction mixture, or by maintaining the reaction mixture under a non-oxygen atmosphere, such as an atmosphere comprising an inert gas, e.g., argon, or by maintaining the reaction mixture in a reaction vessel that contains no headspace as described in Section I above.

The compositions of the invention can be made by obtaining a bacterial extract, obtaining a nucleic acid encoding the desired protein, and combining the bacterial extract, the nucleic acid, labeled and/or unlabeled methionine, and optionally a reducing agent (or agents), to form a reaction mixture, and optionally regulating the $DO_2$ concentration in the reaction mixture, by any of the methods described in Sections I and III above.

In a preferred embodiment, the composition comprises an additional component or combination of components in the reaction mixture, and/or an enhanced concentration of a component or combination of components in the reaction mixture, which improves the reaction mixture's in vitro transcription and/or translation capabilities. Suitable types and concentrations of such components are described in Section I(3) above, and can be obtained and incorporated into the compositions of the invention by any of the methods described in Section I(3) above.

In a preferred embodiment, the composition of the invention further comprises a desired protein-encoding DNA at a concentration of about 0.05 mg/ml to about 1.2 mg/ml, an initial unlabeled methionine concentration of about 0.1 mM to about 2.0 mM, a bacterial cell-free extract derived from a pure culture of an *E. coli* bacterium, and a polyethylene glycol with an average molecular weight of about 6,000 D (PEG-6000) at a concentration of about 1 percent (w/v) to about 5 percent (w/v).

Further details of the invention can be found in the following examples, which further define the scope of the invention. All references cited herein are expressly incorporated by reference in their entirety.

EXAMPLE 1

Materials and Methods

A. Cell lysate preparation

Extracts, designated S135, were prepared from strain 27C7 (W3110, tonA, phoA E15, (argF-lac) 169, ptr3, degP41, ompT, kan') (U.S. Pat. No. 5,288,931, ATCC No. 55,244) and strain 27C7 expressing phGH4R (27C7 (phGH4R)) (Chang et al., *Gene*, 55: 189–196 (1987)). The original procedure by Zubay (1973) and a modified version (Pratt, et al, 1981) were employed for extract preparation. Essentially, RNase-free conditions were maintained throughout. Cell paste was obtained from 10 liter (L) fermentation cultures. A 200 gram (g) sample of cell paste was washed three times with 500 milliliters (ml) of S30 buffer (0.01 M Tris-acetate, pH 8.2, 0.014 M magnesium acetate, 0.06 M potassium acetate, 0.001 M DTT). The final resuspension was in S30 buffer containing 0.005% 2-mercaptoethanol, at 100 ml per 10 g of cells. The suspension was centrifuged at 16,000 times gravity (xg) for 30 minutes (min.) at 4° C. and resuspended slowly in 63.5 ml S30 buffer per 50 g cells. The cells were then lysed in a French press at 8400 pounds per square inch (psi) and supplemented with 100 microliters (ml) of 0.1 M DTT per 10 ml of cell lysate collected. The preparation was then immediately centrifuged at 30,000×g for 30 min. at 4° C. The upper four-fifths of the supernatant was recentrifuged at 30,000×g for 30 min. at 4° C. and again the upper four fifths of the supernatant was collected. These consecutive centrifugations allowed the removal of large contaminating DNA fragments. The extract at this point was incubated with a collection of components which are referred to herein as the pre-incubation mix (6.6 units/milliliter (u/ml) of pyruvate kinase, 5 mM magnesium acetate, 7.8 mM ATP, 50 mM phosphoenolpyruvate, 2.6 mM DTT, 2.4 mM 19 amino acids (all amino acids except methionine)). Incubation was conducted in an orbital shaker at 37° C for 80 min. using 7.5 ml of pre-incubation mix per 25 ml of extract supernatant. The extract was then dialyzed extensively against 50 volumes of S30 buffer at 4° C., with 3 changes at 45 min. intervals. This was followed by centrifugation at 150,000×g for 2.5 hours (hr) to remove contaminating membranes. The extract was then aliquoted and stored at −70° C. The protein concentration was estimated by using spectrophotometric measurements of light absorbance at 260 nm and 280 nm in the correlation method of Elayne, *Meth Enzymol.*, 3: 447 (1957).

B. Isolation of DNA

27C7(phGH4R) cells were grown overnight in a broth culture containing 250 ml of Luria broth (LB) with 50 $\mu$g/ml tetracycline. Cells were recovered from the broth culture by centrifugation and resuspended in 3 ml of an ice-cold solution of 25% sucrose in 50 mM Tris-HCl at pH 8.0. 0.5 ml of a lysozyme solution (10 mg/ml lysozyme in 50 mM Tris-HCl at pH 8.0) was added to the cell suspension, and the mixture was incubated on ice for 15 minutes. Next, 1.0 ml of 0.25 M EDTA solution (pH 8.0) was added and the mixture was incubated on ice for an additional 15 minutes. To lyse the cells, 4 ml of 2% Triton X-100 in 50 mM Tris-HCl, 0.0625 M EDTA, pH 8.0 was added to the mixture. Cell debris was removed from the lysate by centrifugation. The centrifugation supernatant was recovered and combined with 2 volumes of 0.2 M NaOH, 1% SDS, mixed by swirling and incubated on ice for 5 minutes. One volume of 2 M potassium acetate (KOAc), 2 M acetic acid was added and the mixture was incubated on ice for another 5 minutes. The mixture was centrifuged to help remove contaminating protein precipitates. The centrifugation supernatant was mixed with 2 volumes of ethanol and incubated at −20° C. for 1–2 hours to precipitate DNA. Following incubation, the DNA precipitate mixture was centrifuged to recover a DNA pellet. The DNA pellet was resuspended in 0.4 ml TE buffer, 1% SDS. The resuspended DNA was loaded onto a sepharose CL 4B/2B column equilibrated with a solution of TE buffer (10 mM Tris-HCl, pH 7.5, 1 mM EDTA) containing 1% SDS and was eluted from the column with the same solution. 800 $\mu$l fractions of column eluate were collected, and the peak DNA fractions were determined by spectrophotometric absorbance at 260 nm and confirmed by agarose gel electrophoresis. The peak fractions were pooled and stored at 4° C.

C. Transcription-Translation

A typical transcription-translation reaction mixture contained 1.5–2.0 micrograms ($\mu$g) of plasmid DNA, 56.4 mM TAE, 1.76 mM DTT, 0.85 mM each of CTP, GTP, and UTP, 27 mM PEP, 0.35 mM 19 amino acids (all amino acids except methionine), 1.9% PEG-6000, 18–35 $\mu$g/ml folinic acid, 27 $\mu$g/ml folic acid, 27 $\mu$g/ml NADP$^+$, 27 $\mu$g/ml FAD, 27 $\mu$g/ml pyroxidine HCl, 11 $\mu$g/ml PABA, 0.34–0.64 mM 3', 5'-cAMP, 0.17 mg/ml tRNAs, 36.0 mM ammonium acetate, 72.0 mM potassium acetate, 9.7 mM calcium acetate, 6.7 mM magnesium acetate, 45 units of T7 RNA polymerase, 20 microcuries ($\mu$Ci) of 1000 curies/millimole (Ci/mmol) [$^{35}$S]-methionine, and 2–8 $\mu$l of the S135 extract (148 $\mu$g/$\mu$l),wherein the final volume was adjusted to 30 $\mu$l, pH 7.0. Incubation was conducted in a water bath set at 37° C. for 60 min. followed by the addition of 10 $\mu$l of cold (unlabeled) methionine (8 mg/ml) to complete polypeptide chains. After a further 5 min. of protein synthesis the reaction was terminated by incubation on ice for 10 min.

For estimation of the [$^{35}$S]methionine incorporation into protein, 2 $\mu$l to 5 $\mu$l aliquots of the incubation mixture were transferred to numbered disks of Whatmann 3 MM filter paper and allowed to dry at room temperature. Each filter was submerged in an ice-cold 200 ml solution of 10% TCA and 0.1% methionine. The solutions were incubated on ice, with occasional swirling, for one hour. Each of the filters was then transferred to a 200 ml solution of 5% TCA and 0.1% methionine and incubated at 90° C. for 10 min. The 5% TCA/0.1% methionine wash was decanted from each filter and replaced with fresh, ice-cold 5% TCA/0.1% methionine solution. The 5% TCA/0.1% methionine wash was changed 3 or 4 times at 15 minute intervals for each filter. After the last wash was decanted, acetone was added until each filter was covered. The filters were briefly swirled in the acetone and the acetone was decanted. The filters were removed with forceps from the washes and allowed to dry at room temperature. Each dried filter was placed in a separate scintillation vial with scintillation fluid and then assayed for radioactivity in a scintillation counter.

The TCA-precipitable material was also analyzed by gel electrophoresis. 30 $\mu$l of 10 mM Tris-acetate, pH 7.0 and 30 $\mu$l of sample buffer (containing 20% glycerol, 2% sodium dodecylsulfate (SDS), 0.125 M Tris(hydroxymethyl) aminomethane hydrochloride (Tris-HCl), 5% 2-mercaptoethanol, 0.001% (w/v) Bromophenol blue, pH 6.8) were added to the remainder of the incubation mixture. The sample was boiled for 3 minutes and loaded onto a 4–20% Tris-glycine gel.

Results

A. Effect of various Mg$^{2+}$ concentrations using 0.05 micrograms/microliter($\mu$g/$\mu$l) DNA Among the concentrations tested, the best results were seen in the presence of 6.7 mM Mg$^{2+}$. Gel electrophoresis of the in vitro transcription-translation products detected a major band at approximately 23 kilodaltons (kD), the molecular weight of the precursor form of secreted human growth hormone (hGH), and bands of lesser intensity at approximately 32 kD, 20 kD, 14 kD and 7 kD.

B. Effect of increasing DNA concentrations

An increase in the amount of plasmid (phGH4R)-encoded proteins, hGH and β-lactamase, was seen by simply increasing the concentration of DNA added to a standard reaction, containing 6 mg/ml of S135. In FIG. 1, the effect of DNA concentration on total protein synthesis is depicted as the amount of TCA-precipitable material recovered at various DNA concentrations. Lane 2 represents a typical reaction with 0.06 $\mu$g/$\mu$l plasmid (phGH4R) DNA at the end of one hour, while lane 3 depicts the increase in protein synthesis at an increased DNA concentration at the end of one and four hours of incubation. Addition of an RNase inhibitor to the translation reaction was slightly beneficial (lane 4), but increasing the DNA concentration beyond 1.4 $\mu$g/$\mu$l produced no further benefit (lanes 5 and 6). Also, incubation over a longer period of time (four hours) led to a drop in the total protein detected as compared to the amount at the end of one hour, suggesting some degradation.

The amount of plasmid DNA present in a typical *E coli*, assuming 30 copies per cell, was estimated to be approximately 0.28 $\mu$g/$\mu$l. A concentration close to this value was used in the next set of reactions unless otherwise stated.

C. Preferred reactions using 0.28 μg/μl DNA

I. Magnesium

A range of dicationic magnesium concentrations between 0 and 6.5 mM were tested and a preferred concentration was established to be approximately 5.3 mM (FIG. 2). A S135 concentration of 8 mg/ml was used in this set of reactions.

II. Cell lysate (S135)

A range of S135 concentrations representing 0 to 10 mg/ml of cytoplasmic protein were tested. Previous work with 0.06 μg/μl DNA had shown that concentrations above 8 mg/ml S135 could be inhibitory to translation. Nevertheless, in reactions with a DNA concentration of 0.28 μg/μl, S135 concentrations up to 10 mg/ml were found to be stimulatory (FIG. 3).

III. Time course of protein translation

The rate of protein synthesis was compared between reactions containing low (0.06 μg/μl) and high (0.23 μg/μl) levels of DNA. Aliquots were removed at 10 min. intervals over a one hour period and processed for TCA-precipitable material. The results are illustrated in FIG. 4. Clearly, the rates of synthesis over the first 20 min. are very different; the amount of $7.5 \times 10^5$ counts per minute (cpm) for the high level of DNA was much higher than the amount of $1.9 \times 10^5$ cpm obtained for the low level of DNA. In both cases synthesis is linear for only the first 20 mins., with the precipitable protein concentration dropping slightly after that time by 19% and 24% for low and high levels of DNA, respectively. Table 1 below summarizes the results obtained in the preferred in vitro system described above as compared to in vivo expression rates obtained with *E. coli* 27C7 (phGH4R).

TABLE 1

SUMMARY

|  | plasmid DNA (μg/μl) | Expression Rates (μg protein/mg cytop.prot.hr.) |
|---|---|---|
| in vivo | 0.28 (30 copies/cell) | 10–30 |
| in vitro | 0.06 | 0.03 |
| increased DNA | 0.23 | 0.17 |
| optimized | 0.23 | 0.72 |

EXAMPLE 2

Materials and Methods

Two sets of reaction mixtures were prepared with 0.23 μg/μl phGH4R DNA, 6 mM $Mg^{2+}$ acetate, 12 mg/ml S135 extract, and with all other components in the amounts and concentrations described in Example 1 above. The first set of reactions was carried out according to the procedures described in Example 1 above. The same procedures were used for the second set of reactions except that the Eppendorf tubes containing the reaction mixtures were sparged carefully with argon and an argon overlay was maintained during the reactions.

Results

As shown in FIG. 5, the second set of reactions continued to produce new protein for 50 minutes and yielded approximately $1.5 \times 10^6$ cpm of TCA-precipitable protein whereas the first set of reactions produced new protein for only 20 minutes and yielded a total of approximately $0.7 \times 10^6$ cpm of TCA-precipitable protein. Thus, the reduced dissolved oxygen ($DO_2$) concentration in the second set of reactions allowed the reaction to continue over twice as long and to produce more than twice as much new protein as the first set of reactions.

EXAMPLE 3

Materials and Methods

A series of reaction mixtures was prepared with 0.28 μg/μl phGH4R DNA, 12 mg/ml S135 extract, 0.55 mM for each of the 19 amino acids other than methionine, 0.6 to 3.3 micromoles/liter (EM) [$^{35}$S]methionine, and with all other components in the amounts and concentrations described in Example 1 above. The reactions were carried out according to the procedures described in Example 1 above.

A second series of reaction mixtures was prepared with 1.2 μg/μl phGH4R DNA, 12 mg/ml S135 extract, 5% PEG-6000, 44.6 μg/ml folinic acid, 27 μg/ml $NADP^+$, 27 μg/ml FAD, 27 μg/ml pyridoxine HCl, 11 μg/ml PABA, 1.50 mM DTT, 0.17 mg/ml tRNAs, 2.7 units/μl T7 RNA polymerase, 0.35 mM of each amino acid except methionine, 27 mM PEP, 0.85 mM each of CTP, UTP and GTP, 1.22 mM ATP, 56.4 mM TAE (pH 8.2), 0.0043 mM to 1.78 mM methionine, and with all other components in the amounts and concentrations described in Example 1 above. Each mixture was prepared to contain 0.0043 mM [$^{35}$S] methionine and any additional methionine concentration was provided by unlabeled methionine to avoid excess radioactivity in the mixture.

A third series of reaction mixtures was prepared with 0.28 μg/μl or 0.84 μg/μl phGH4R DNA, 7 to 82 mg/ml S135 extract, 3.3 μM [$^{35}$S]methionine and all other components in the amounts and concentrations described in Example 1 above. The reactions were carried out according to the procedures described above in Example 1.

Results

Many factors were tested for their effect and preferred levels were determined for those factors found to exert some influence on reaction efficiency. A retrospective summary of the results leading to the total increase in initial synthesis rate is presented in Table 2 below. The initial synthesis rate with the optimal [$Mg^{2+}$] of 5.2 mM was used as the 1 × basis of comparison.

TABLE 2

| Change | Fold Improvement |
|---|---|
| Increase DNA from 0.05 to 0.84 μg/μl | 8x |
| Increase $^{35}$S Met from 0.6 to 3.3 μM | 3x |
| Increase Initiation Factors | 1.5x |
| Increase PEG from 1.9% to 5% | 1.5x |
| Increase Methionine from 4.3 μM to 1.8 mM | 14x |
| Synergistic Effects | 1.1x |
| Total | 850x |

The set of reactions in which the [$^{35}$S]methionine concentration was varied from 0.6 to 3.3 μM produced the results shown in FIG. 6. These results are the TCA-precipitable counts obtained after one hour of reaction and indicated that the system reached a plateau in TCA-precipitable counts at a [$^{35}$S]methionine concentration of approximately 1.5 μM. Other reactions suggested a slight additional benefit at 3.3 μM [$^{35}$S]methionine and this concentration was used for some of the optimization studies herein.

The series of reactions in which higher concentrations of methionine were tested with 5% PEG, 1.2 μg/μl DNA, and higher concentrations of "initiation factors" produced the results shown in Table 3 below. In the evaluation of the results, a careful accounting was done to determine the fraction of the added radioactivity that became TCA-precipitable. This fraction was then multiplied by the total methionine added to determine the amount of methionine incorporated into protein. In the calculation of protein produced, it was assumed that the bulk of the product was prehGH with five methionine residues and a molecular weight of 23,000 D.

achieved at the cost of lower specific rates. Table 4 below presents a summary of the data obtained for the case of maximum specific rate and the case of maximum volumetric rate and compares these to estimated in vivo rates.

TABLE 4 in vitro Protein Synthesis rates with *E. coli* Extracts
(Rates based on TCA-precipitable Counts with $^{35}$S Methionine and expressed as prehGH Equivalents)

| | The Target: In vivo Rates | Literature Method (Pratt, Zubay) | Under Conditions For Best Spec. Rate | Under Conditions For Best Vol. Rates |
|---|---|---|---|---|
| Specific Rate ($\mu$g/mg cytopl. prot.-hr) | 12 | 0.038 | 32 | 5.8 |
| Volumetric Rate ($\mu$g/ml-hr) | 1500 | 0.3 | 210 | 320 |
| DNA Util. Rate ($\mu$g/mg DNA-hr) | 20,690 | 6 | 760 | 380 |

TABLE 3

| [met] (mM) | Initial Rate ($\mu$g protein/mg cytopl. prot.-hr) |
|---|---|
| 0.0043 | 2.3 |
| 0.143 | 5.5 |
| 0.267 | 9.0 |
| 0.534 | 13.7 |
| 1.07 | 25.4 |
| 1.78 | 32.3 |

FIG. 7 presents a Lineweaver-Burke plot of the full data set. FIG. 8 shows the data set with the omission of the lowest methionine concentration. FIG. 7 portrays two separate regions of dependence on the concentration of methionine for in vitro protein synthesis with an *E. coli* cell extract. The region at low methionine concentration was near the $k_m$ of the methionyl tRNA$_m^{Met}$ synthetase (apparent affinity of 20 $\mu$M). However, the region above 0.1 mM showed a surprising dependence on higher concentrations of methionine. These data indicated Michaelis-Menton kinetics with a km of 1 mM and a $v_{max}$ of approximately 50 micrograms protein/milligrams cytoplasmic protein-hour ($\mu$g/mg cytopl. prot.-hr). The discovery of the dependence on higher methionine concentrations resulted in an approximately 14 fold increase in the initial specific rate of protein synthesis.

The set of reactions in which higher concentrations of S135 extract were tested with 0.28 or 0.83 mg/ml of phGH4R DNA (the third set of reactions) produced the results shown in FIGS. 9 and 10. These data are measurements of volumetric and specific rates of protein synthesis as a function of the *E. coli* S135 extract concentration.

At the higher concentrations of cell extract, non-specific precipitation of labeled methionine was observed. Therefore, control incubations were conducted without plasmid DNA addition to determine the background counts. The background counts were subtracted from the TCA-precipitated counts measured in the synthesis reactions to yield the counts incorporated by newly synthesized protein. These data showed that higher volumetric synthesis rates were achieved with more cell extract at the 0.83 mg/ml DNA concentration. However, these higher volumetric rates were In conclusion, very high specific rates of protein expression were obtained in vitro using preferred conditions with *E. coil* extracts. The in vitro rates obtained rival or exceed the in vivo rates of specific expression of a single recombinant protein.

We claim:

1. A method for in vitro protein synthesis comprising
   (1) expressing a nucleic acid encoding a desired protein in a reaction mixture comprising a bacterial cell-free extract maintained in a reaction vessel under an atmosphere occupying the headspace of the reaction vessel, wherein the reaction mixture further comprises a reducing agent and dissolved oxygen ($DO_2$) wherein the $DO_2$ concentration is regulated by using a reduced oxygen concentration in the atmosphere such that complete oxidation of the reducing agent concentration does not occur for a period of at least about 30 minutes following initiation of protein synthesis in the reaction mixture; and
   (2) recovering the desired protein from the reaction mixture.

2. The method of claim 1 wherein the reaction mixture is maintained under a non-oxygen atmosphere.

3. The method of claim 2 wherein the non-oxygen atmosphere comprises an inert gas.

4. The method of claim 3 wherein the inert gas is argon.

5. The method of claim 1 wherein complete oxidation of the reducing agent concentration does not occur for a period of at least about 60 minutes following initiation of protein synthesis in the reaction mixture.

6. The method of claim 5 wherein complete oxidation of the reducing agent concentration does not occur for a period of at least about two hours following initiation of protein synthesis in the reaction mixture.

7. The method of claim 1 wherein the reducing agent is dithiothreitol.

8. The method of claim 7 wherein the reducing agent concentration is about 1.3 mM to about 1.8 mM.

9. The method of claim 8 wherein the reaction mixture is maintained in a closed reaction vessel with a headspace containing an atmosphere comprising oxygen, the initial $DO_2$ concentration in the reaction mixture no greater than about 0.25 mM, and the oxygen content in the atmosphere is less than an amount sufficient to increase by about 0.75 mM the $DO_2$ concentration in the reaction mixture upon complete transfer of the atmospheric oxygen to liquid phase in the reaction mixture.

10. The method of claim 1 wherein the bacterial cell-free extract is derived from a pure culture of a Gram-negative bacterium.

11. The method of claim 10 wherein the bacterium is *E. coli*.

12. A composition for in vitro protein synthesis comprising a reaction mixture comprising a bacterial cell-free extract and a nucleic acid encoding a desired protein maintained in a reaction vessel under an atmosphere occupying the headspace of the reaction vessel, wherein the reaction mixture further comprises a reducing agent and dissolved oxygen ($DO_2$) wherein the $DO_2$ concentration is regulated by using a reduced oxygen concentration in the atmosphere such that complete oxidation of the reducing agent concentration does not occur for a period of at least about 30 minutes following initiation of protein synthesis in the reaction mixture.

13. The composition of claim 12 wherein the reaction mixture is under a non-oxygen atmosphere.

14. The composition of claim 13 wherein the non-oxygen atmosphere comprises an inert gas.

15. The composition of claim 14 wherein the inert gas is argon.

16. A method for in vitro protein synthesis comprising
 (1) expressing a nucleic acid encoding a desired protein in a reaction mixture comprising a bacterial cell-free extract and an initial methionine (Met) concentration of at least about 1.0 mM; and
 (2) recovering the desired protein from the reaction mixture.

17. The method of claim 16 wherein the reaction mixture comprises an initial methionine (Met) concentration of about 1.0 mM to about 2.0 mM.

18. The method of claim 16 wherein the bacterial cell-free extract is derived from a pure culture of a Gram-negative bacterium.

19. The method of claim 18 wherein the bacterium is *E. coli*.

20. A method for in vitro protein synthesis comprising
 (1) expressing a nucleic acid encoding a desired protein in a reaction mixture comprising a bacterial cell-free extract, labeled methionine, and unlabeled methionine, wherein the initial concentration of unlabeled methionine is at least about 0.1 mM; and
 (2) recovering the desired protein from the reaction mixture.

21. The method of claim 20 wherein the initial concentration of unlabeled methionine is about 0.1 mM to about 2.0 mM.

22. The method of claim 20 wherein the bacterial cell-free extract is derived from a pure culture of a Gram-negative bacterium.

23. The method of claim 22 wherein the bacterium is *E. coli*.

24. A composition for in vitro protein synthesis comprising a reaction mixture comprising a bacterial cell-free extract, a nucleic acid encoding a desired protein, and an initial methionine concentration of at least about 1.0 mM.

25. A composition for in vitro protein synthesis comprising a reaction mixture comprising a bacterial cell-free extract, a nucleic acid encoding a desired protein, labeled methionine, and unlabeled methionine, wherein the initial concentration of unlabeled methionine is at least about 0.1 mM.

* * * * *